United States Patent [19]

Frenken et al.

[11] Patent Number: 6,114,147
[45] Date of Patent: Sep. 5, 2000

[54] IMMOBILIZED PROTEINS WITH SPECIFIC BINDING CAPACITIES AND THEIR USE IN PROCESSES AND PRODUCTS

[75] Inventors: Leon Gerardus J. Frenken, Rotterdam; Pieter de Geus, Barendrecht; Franciscus Maria Klis, Amsterdam, all of Netherlands; Holger York Toschka, Reken, Germany; Cornelis Theodorus Verrips, Maassluis, Netherlands

[73] Assignee: Unilever Patent Holdings, Netherlands

[*] Notice: This patent is subject to a terminal disclaimer.

[21] Appl. No.: 08/971,692

[22] PCT Filed: Feb. 10, 1994

[86] PCT No.: PCT/EP94/00427
§ 371 Date: Nov. 1, 1995
§ 102(e) Date: Nov. 1, 1995

[87] PCT Pub. No.: WO94/18330
PCT Pub. Date: Aug. 18, 1994

Related U.S. Application Data

[63] Continuation of application No. 08/492,114, filed as application No. PCT/EP94/00427, Feb. 10, 1994, abandoned.

[30] Foreign Application Priority Data

Feb. 10, 1993 [NL] Netherlands ............... 93200350

[51] Int. Cl.[7] ............. C12P 21/04; G01N 33/53; C12N 1/14; C07H 21/04
[52] U.S. Cl. ............. 435/69.7; 435/7.1; 435/69.8; 435/69.9; 435/254.11; 435/254.2; 536/23.1; 536/23.4; 536/23.7; 536/23.74; 530/350
[58] Field of Search ............ 435/69.7, 69.8, 435/69.9, 320.1, 240.2, 254.27, 7.1; 536/23.1, 23.7, 23.4, 23.74; 530/350; 935/28, 37, 69; 436/501

[56] References Cited

U.S. PATENT DOCUMENTS

| | | | |
|---|---|---|---|
| 5,223,408 | 6/1993 | Goeddel et al. | 435/69.3 |
| 5,223,409 | 6/1993 | Ladner et al. | 435/69.7 |
| 5,602,034 | 2/1997 | Tekamp-Olson | 435/254.11 |
| 5,618,290 | 4/1997 | Robinson et al. | 530/387.1 |

FOREIGN PATENT DOCUMENTS

| | | |
|---|---|---|
| 244221 | 11/1987 | European Pat. Off. . |
| 0474891 | 3/1992 | European Pat. Off. . |
| 92 20805 | 11/1982 | WIPO . |
| 92 04363 | 3/1992 | WIPO . |
| 94 01567 | 1/1994 | WIPO . |

OTHER PUBLICATIONS

Lipke et al., Mol. Cell, Biol. 9: 3155–3165, (Aug. 1989).

*Primary Examiner*—Carla J. Myers
*Assistant Examiner*—Diana Johannsen
*Attorney, Agent, or Firm*—Cushman Darby & Cushman IP Group of Pillsbury Madison & Sutro

[57] ABSTRACT

A method is provided for immobilizing a binding protein capable of binding to a specific compound, using recombinant DNA techniques for producing said binding protein or a functional part thereof. The binding protein is immobilized by producing it as part of a chimeric protein also comprising an anchoring part derivable from the C-terminal part of an anchoring protein, thereby ensuring that the binding protein is localized in or at the exterior of the cell wall of the host cell. Suitable anchoring proteins are yeast α-agglutinin, FLO1 (a protein associated with the flocculation phenotype in *S. cerevisiae*), the Major Cell Wall Protein of lower eukaryotes, and a proteinase of lactic acid bacteria. For secretion the chimeric protein can comprises a signal peptide including those of α-mating factor of yeast, α-agglutinin of yeast, invertase of Saccharomyces, inulinase of Kluyveromyces, α-amylase of Bacillus, and proteinase of lactic acid bacteria. Also provided are recombinant polynucleotides encoding such chimeric protein, vectors comprising such polynucleotide, transformed microorganisms having such chimeric protein immobilized on their cell will, and a process for carrying out an isolation process by using such transformed host, wherein a medium containing said specific compound is contacted with such host cell to form a complex, separating said complex from the medium and, optionally, releasing said specific compound from said binding protein.

8 Claims, 12 Drawing Sheets

(2 of 12 Drawing Sheet(s) Filed in Color)

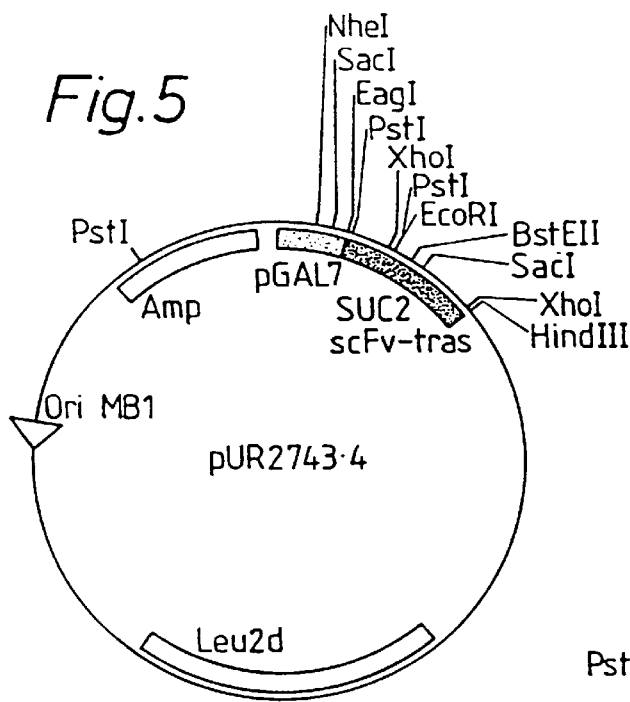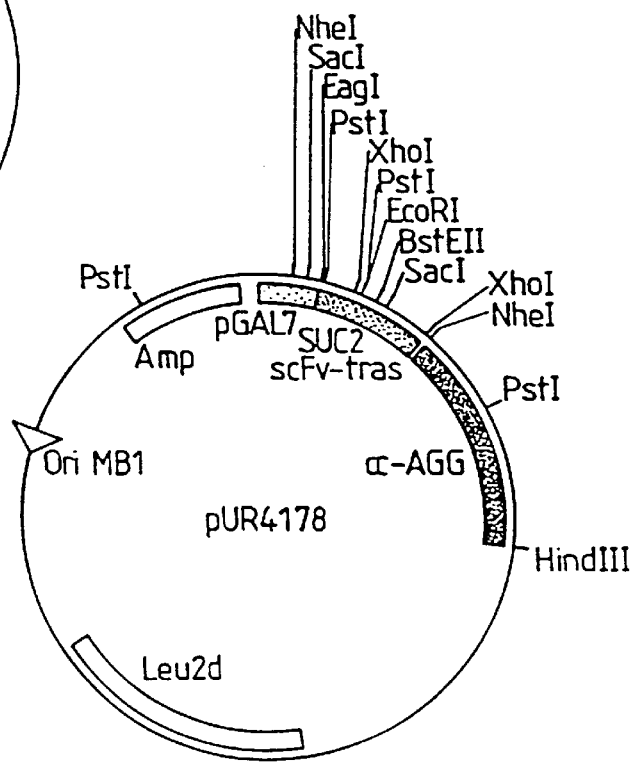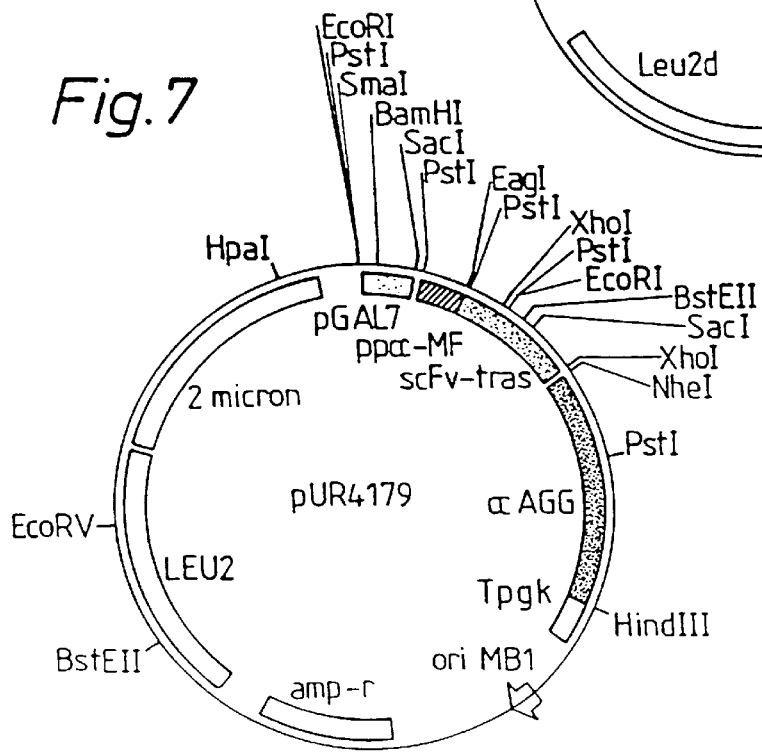

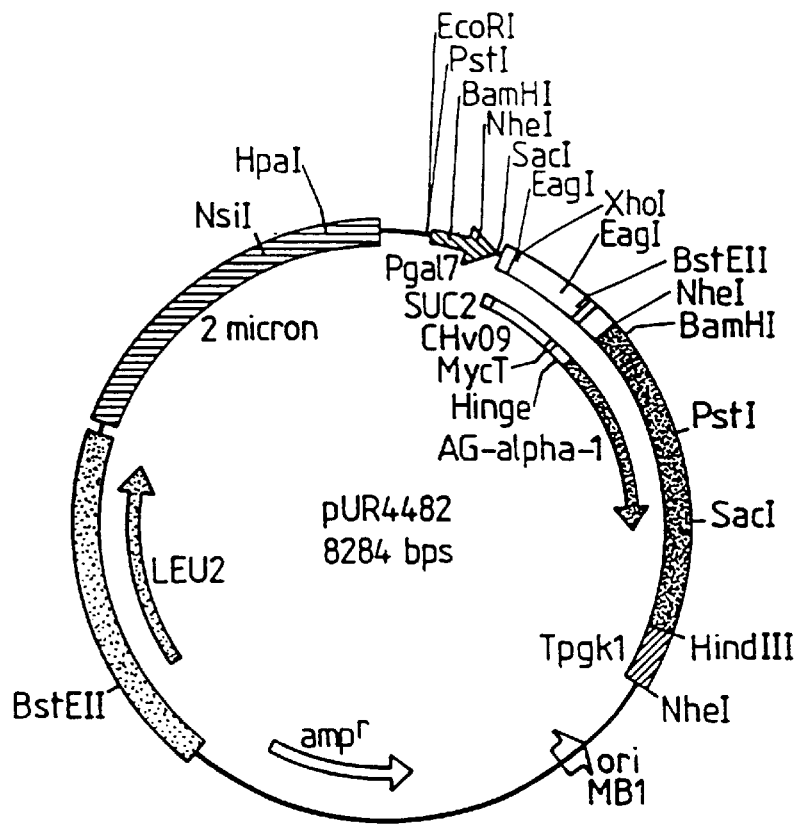
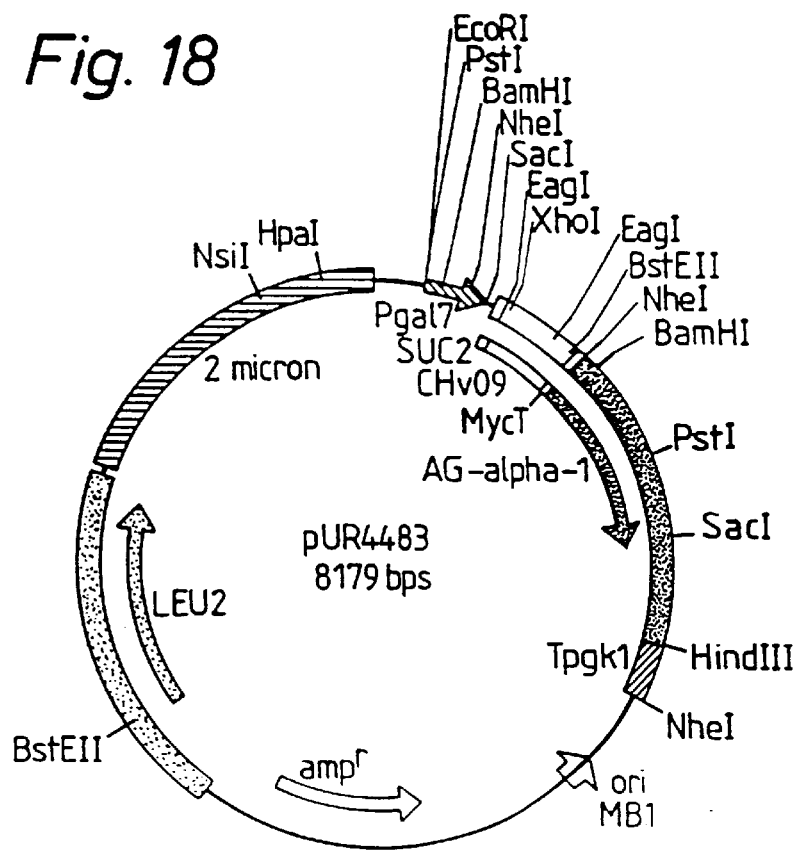
Fig. 18

Figure 19
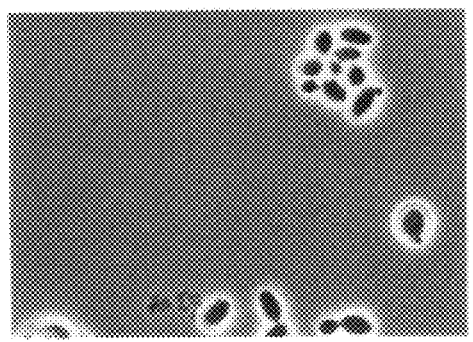
pUR4424
Ph + Fl
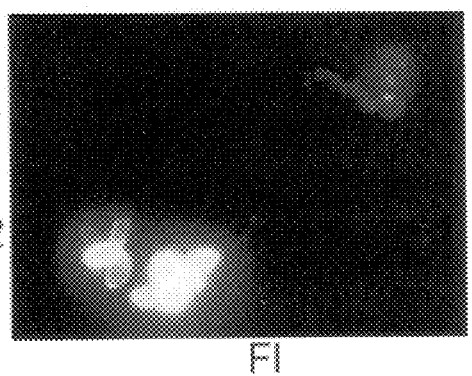
pUR4482
Ph + Fl          Fl
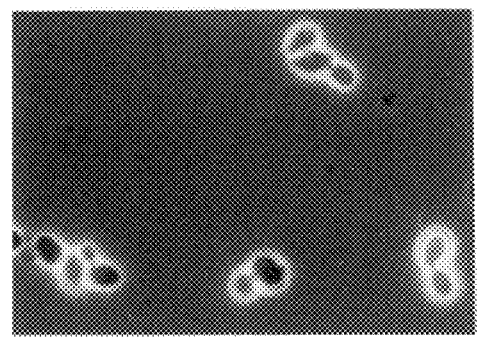 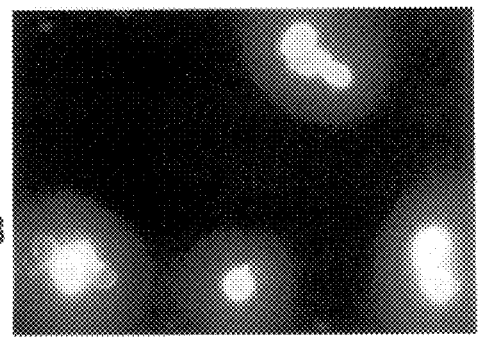
pUR4483
Ph + Fl          Fl Figure 20
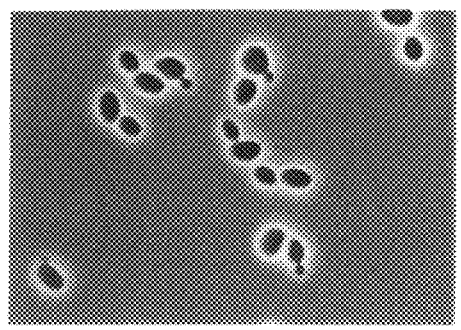
pUR4424
Ph + Fl
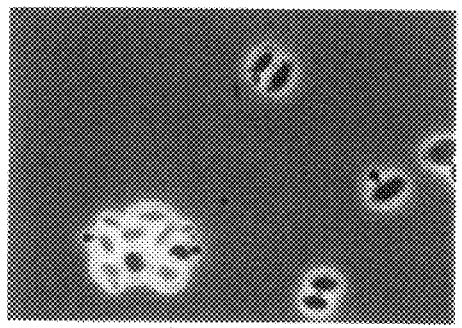 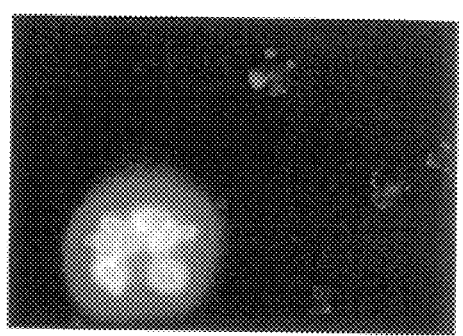
pUR4482
Ph + Fl            Fl
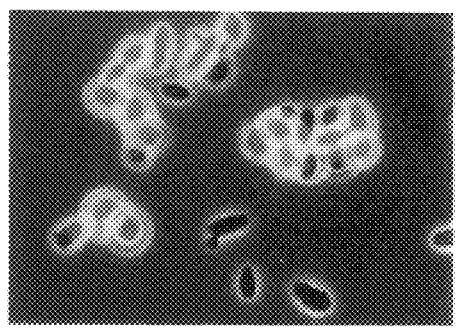 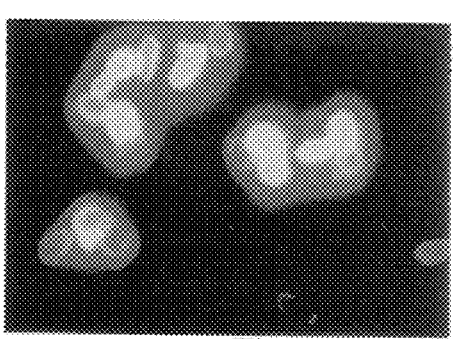
pUR4483
Ph + Fl            Fl

SEQUENCE LISTING (1) GENERAL INFORMATION:

(iii) NUMBER OF SEQUENCES: 40

(2) INFORMATION FOR SEQ ID NO: 1:

(i) SEQUENCE CHARACTERISTICS:
        (A) LENGTH: 231 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: fragment in pUR4119

(xi) SEQUENCE DESCRIPTION: SEQ ID NO: 1:

```
GAATTCGAGC TCATCACACA AACAAACAAA ACAAAATGAT GCTTTTGCAA GCCTTTCTTT      60

TCCTTTTGGC TGGTTTTGCA GCCAAAATAT CTGCGCAGGT GCAGCTGCAG TAATGAACCA     120

CGGTCACCGT CTCCTCAGGT GGAGGCGGTT CAGGCGGAGG TGGCTCTGGC GGTGGCGGAT     180

CGGACATCGA GCTCACTCAG ACCAAGCTCG AGATCAAACG GTGATAAGCT T              231
```

(2) INFORMATION FOR SEQ ID NO: 2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:

(B) CLONE: linker XhoI-NheI coding strand (xi) SEQUENCE DESCRIPTION: SEQ ID NO: 2:

TCGAGATCAA AGGCGGATCT G                                              21

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: linker XhoI-NheI non-coding strand (xi) SEQUENCE DESCRIPTION: SEQ ID NO: 3:

CTAGCAGATC CGCCTTTGAT C                                              21

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: linker EagI-PstI coding strand (xi) SEQUENCE DESCRIPTION: SEQ ID NO: 4:

GGCCGCCCAG GTGCAGCTGC A                                              21

(2) INFORMATION FOR SEQ ID NO: 5:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: linker EagI-PstI non-coding strand (xi) SEQUENCE DESCRIPTION: SEQ ID NO: 5:

GCTGCACCTG GGC                                                       13

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: PCR primer A (heavy chain)

(xi) SEQUENCE DESCRIPTION: SEQ ID NO: 6:

AGGTSMARCT GCAGSAGTCW GG                                             22

(2) INFORMATION FOR SEQ ID NO: 7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: PCR primer B (heavy chain)

(xi) SEQUENCE DESCRIPTION: SEQ ID NO: 7:

```
TGAGGAGACG GTGACCGTGG TCCCTTGGCC CC                          32
```

(2) INFORMATION FOR SEQ ID NO: 8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: PCR primer C (light chain)

(xi) SEQUENCE DESCRIPTION: SEQ ID NO: 8:

```
GACATTGAGC TCACCCAGTC TCCA                                   24
```

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: PCR primer D (light chain)

(xi) SEQUENCE DESCRIPTION: SEQ ID NO: 9:

```
GTTTGATCTC GAGCTTGGTC CC                                     22
```

(2) INFORMATION FOR SEQ ID NO: 10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: linker EcoRI-PstI coding strand (xi) SEQUENCE DESCRIPTION: SEQ ID NO: 10:

```
AATTCGGCCG TTCAGGTGCA GCTGCA                                 26
```

(2) INFORMATION FOR SEQ ID NO: 11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
             (B) CLONE: linker EcoRI-PstI non-coding strand (xi) SEQUENCE DESCRIPTION: SEQ ID NO: 11:

GCTGCACCTG AACGGCCG                                                    18

(2) INFORMATION FOR SEQ ID NO: 12:

(i) SEQUENCE CHARACTERISTICS:
             (A) LENGTH: 714 base pairs
             (B) TYPE: nucleic acid
             (C) STRANDEDNESS: double
             (D) TOPOLOGY: linear (ii) MOLECULE TYPE: DNA (genomic)

(vii) IMMEDIATE SOURCE:
             (B) CLONE: ScFv antitraseolide 02/01/01

(xi) SEQUENCE DESCRIPTION: SEQ ID NO: 12:

CTGCAGGAGT CTGGACCTGG CCTGGTGAAA CCTTCTCAGT CTCTGTCCCT CACCTGCACT        60

GTCACTGGCT ACTCAATCAC CAGTGATTTT GCCTGGAACT GGATCCGGCA GTTTCCAGGA       120

AACCAACTGG AGTGGATGGG CTACATAAGC TACAGTGGTA GCACTAGCTA CAACCCATCT       180

CTCAAAAGTC GAATCTCTCT CACTCGAGAC ACATCCAAGA ACCAGTTCTT CCTGCAGTTG       240

AATTCTGTGA CTACTGAGGA CACAGCCACA TATTACTGTG CAACGTCCCT AACATGGTTA       300

CTACGTCGGA AACGTTCTTA CTGGGGCCAA GGGACCACGG TCACCGTCTC CTCAGGTGGA       360

GGCGGTTCAG GCGGAGGTGG CTCTGGCGGT GGCGGATCGG ACATCGAGCT CACCCAGTCT       420

CCATCCTCCA TGTCTGTATC TCTGGGAGAC ACAGTCAGCA TCACTTGCCA TGCAAGTCAG       480

GACATTAGCA GTAATATAGG GTGGTTGCAG CAGAAACCAG GAAATCATT TAAGGGCCTG        540

ATCTATCATG GAACCAACTT GGAAGATGGT ATTCCATCAA GGTTCAGTGG CAGTGGATCT       600

GGAGCAGATT ATTCCCTCAC CATCAGCAGC CTGGAATCTG AAGATTTTGC AGACTATTAC       660

TGTGTACAGT ATGCTCAGTT TCCATTCACG TTCGGCTCGG GACCAAGCT CGAG              714

(2) INFORMATION FOR SEQ ID NO: 13:

(i) SEQUENCE CHARACTERISTICS:
             (A) LENGTH: 734 base pairs
             (B) TYPE: nucleic acid
             (C) STRANDEDNESS: double
             (D) TOPOLOGY: linear (ii) MOLECULE TYPE: DNA (genomic)

(vii) IMMEDIATE SOURCE:
             (B) CLONE: ScFv anti-HCG (xi) SEQUENCE DESCRIPTION: SEQ ID NO: 13:

CGGCCGTTCA GGTGCAGCTG CAGGAGTCTG GGGACACTT AGTGAAGCCT GGAGGGTCCC         60

TGAAACTCTC CTGTGCAGCC TCTGGATTCG CTTTCAGTAG CTTTGACATG TCTTGGATTC       120

GCCAGACTCC GGAGAAGAGG CTGGAGTGGG TCGCAAGCAT TACTAATGTT GGTACTTACA       180

CCTACTATCC AGGCAGTGTG AAGGGCCGAT TCTCCATCTC CAGAGACAAT GCCAGGAACA       240

CCCTAAACCT GCAAATGAGC AGTCTGAGGT CTGAGGACAC GGCCTTGTAT TTCTGTGCAA       300

GACAGGGGAC TGCGGCACAA CCTTACTGGT ACTTCGATGT CTGGGGCCAA GGGACCACGG       360

TCACCGTCTC CTCAGGTGGA GGCGGTTCAG GCGGAGGTGG CTCTGGCGGT GGCGGATCGG       420

```
ACATCGAGCT CACCCAGTCT CCAAAATCCA TGTCCATGTC CGTAGGAGAG AGGGTCACCT       480

TGAGCTGCAA GGCCAGTGAG ACTGTGGATT CTTTTGTGTC CTGGTATCAA CAGAAACCAG       540

AACAGTCTCC TAAATTGTTG ATATTCGGGG CATCCAACCG GTTCAGTGGG GTCCCCGATC       600

GCTTCACTGG CAGTGGATCT GCAACAGACT TCACTCTGAC CATCAGCAGT GTGCAGGCTG       660

AGGACTTTGC GGATTACCAC TGTGGACAGA CTTACAATCA TCCGTATACG TTCGGAGGGG       720

GGACCAAGCT CGAG                                                        734
```

(2) INFORMATION FOR SEQ ID NO: 14:

(i) SEQUENCE CHARACTERISTICS:
        (A) LENGTH: 2685 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Saccharomyces cerevisiae (vii) IMMEDIATE SOURCE:
        (B) CLONE: pYY105

(ix) FEATURE:
        (A) NAME/KEY: CDS
        (B) LOCATION: 1..2685
        (D) OTHER INFORMATION: /product= "Flocculation protein"
            /gene= "FLO1"

(xi) SEQUENCE DESCRIPTION: SEQ ID NO: 14:

```
ATG ACA ATG CCT CAT CGC TAT ATG TTT TTG GCA GTC TTT ACA CTT CTG         48
Met Thr Met Pro His Arg Tyr Met Phe Leu Ala Val Phe Thr Leu Leu
 1               5                  10                  15

GCA CTA ACT AGT GTG GCC TCA GGA GCC ACA GAG GCG TGC TTA CCA GCA         96
Ala Leu Thr Ser Val Ala Ser Gly Ala Thr Glu Ala Cys Leu Pro Ala
                20                  25                  30

GGC CAG AGG AAA AGT GGG ATG AAT ATA AAT TTT TAC CAG TAT TCA TTG        144
Gly Gln Arg Lys Ser Gly Met Asn Ile Asn Phe Tyr Gln Tyr Ser Leu
            35                  40                  45

AAA GAT TCC TCC ACA TAT TCG AAT GCA GCA TAT ATG GCT TAT GGA TAT        192
Lys Asp Ser Ser Thr Tyr Ser Asn Ala Ala Tyr Met Ala Tyr Gly Tyr
50                  55                  60

GCC TCA AAA ACC AAA CTA GGT TCT GTC GGA GGA CAA ACT GAT ATC TCG        240
Ala Ser Lys Thr Lys Leu Gly Ser Val Gly Gly Gln Thr Asp Ile Ser
 65                  70                  75                  80

ATT GAT TAT AAT ATT CCC TGT GTT AGT TCA TCA GGC ACA TTT CCT TGT        288
Ile Asp Tyr Asn Ile Pro Cys Val Ser Ser Ser Gly Thr Phe Pro Cys
                 85                  90                  95

CCT CAA GAA GAT TCC TAT GGA AAC TGG GGA TGC AAA GGA ATG GGT GCT        336
Pro Gln Glu Asp Ser Tyr Gly Asn Trp Gly Cys Lys Gly Met Gly Ala
            100                 105                 110

TGT TCT AAT AGT CAA GGA ATT GCA TAC TGG AGT ACT GAT TTA TTT GGT        384
Cys Ser Asn Ser Gln Gly Ile Ala Tyr Trp Ser Thr Asp Leu Phe Gly
        115                 120                 125

TTC TAT ACT ACC CCA ACA AAC GTA ACC CTA GAA ATG ACA GGT TAT TTT        432
Phe Tyr Thr Thr Pro Thr Asn Val Thr Leu Glu Met Thr Gly Tyr Phe
    130                 135                 140

TTA CCA CCA CAG ACG GGT TCT TAC ACA TTC AAG TTT GCT ACA GTT GAC        480
Leu Pro Pro Gln Thr Gly Ser Tyr Thr Phe Lys Phe Ala Thr Val Asp
145                 150                 155                 160

GAC TCT GCA ATT CTA TCA GTA GGT GGT GCA ACC GCG TTC AAC TGT TGT        528
Asp Ser Ala Ile Leu Ser Val Gly Gly Ala Thr Ala Phe Asn Cys Cys
```

-continued

```
Asp Ser Ala Ile Leu Ser Val Gly Gly Ala Thr Ala Phe Asn Cys Cys
            165                 170                 175

GCT CAA CAG CAA CCG CCG ATC ACA TCA ACG AAC TTT ACC ATT GAC GGT       576
Ala Gln Gln Gln Pro Pro Ile Thr Ser Thr Asn Phe Thr Ile Asp Gly
                180                 185                 190

ATC AAG CCA TGG GGT GGA AGT TTG CCA CCT AAT ATC GAA GGA ACC GTC       624
Ile Lys Pro Trp Gly Gly Ser Leu Pro Pro Asn Ile Glu Gly Thr Val
            195                 200                 205

TAT ATG TAC GCT GGC TAC TAT TAT CCA ATG AAG GTT GTT TAC TCG AAC       672
Tyr Met Tyr Ala Gly Tyr Tyr Tyr Pro Met Lys Val Val Tyr Ser Asn
            210                 215                 220

GCT GTT TCT TGG GGT ACA CTT CCA ATT AGT GTG ACA CTT CCA GAT GGT       720
Ala Val Ser Trp Gly Thr Leu Pro Ile Ser Val Thr Leu Pro Asp Gly
225                 230                 235                 240

ACC ACT GTA AGT GAT GAC TTC GAA GGG TAC GTC TAT TCC TTT GAC GAT       768
Thr Thr Val Ser Asp Asp Phe Glu Gly Tyr Val Tyr Ser Phe Asp Asp
                245                 250                 255

GAC CTA AGT CAA TCT AAC TGT ACT GTC CCT GAC CCT TCA AAT TAT GCT       816
Asp Leu Ser Gln Ser Asn Cys Thr Val Pro Asp Pro Ser Asn Tyr Ala
                260                 265                 270

GTC AGT ACC ACT ACA ACT ACA ACG GAA CCA TGG ACC GGT ACT TTC ACT       864
Val Ser Thr Thr Thr Thr Thr Thr Glu Pro Trp Thr Gly Thr Phe Thr
            275                 280                 285

TCT ACA TCT ACT GAA ATG ACC ACC GTC ACC GGT ACC AAC GGC GTT CCA       912
Ser Thr Ser Thr Glu Met Thr Thr Val Thr Gly Thr Asn Gly Val Pro
            290                 295                 300

ACT GAC GAA ACC GTC ATT GTC ATC AGA ACT CCA ACC AGT GAA GGT CTA       960
Thr Asp Glu Thr Val Ile Val Ile Arg Thr Pro Thr Ser Glu Gly Leu
305                 310                 315                 320

ATC AGC ACC ACC ACT GAA CCA TGG ACT GGC ACT TTC ACT TCG ACT TCC      1008
Ile Ser Thr Thr Thr Glu Pro Trp Thr Gly Thr Phe Thr Ser Thr Ser
                325                 330                 335

ACT GAG GTT ACC ACC ATC ACT GGA ACC AAC GGT CAA CCA ACT GAC GAA      1056
Thr Glu Val Thr Thr Ile Thr Gly Thr Asn Gly Gln Pro Thr Asp Glu
            340                 345                 350

ACT GTG ATT GTT ATC AGA ACT CCA ACC AGT GAA GGT CTA ATC AGC ACC      1104
Thr Val Ile Val Ile Arg Thr Pro Thr Ser Glu Gly Leu Ile Ser Thr
            355                 360                 365

ACC ACT GAA CCA TGG ACT GGT ACT TTC ACT TCT ACA TCT ACT GAA ATG      1152
Thr Thr Glu Pro Trp Thr Gly Thr Phe Thr Ser Thr Ser Thr Glu Met
            370                 375                 380

ACC ACC GTC ACC GGT ACT AAC GGT CAA CCA ACT GAC GAA ACC GTG ATT      1200
Thr Thr Val Thr Gly Thr Asn Gly Gln Pro Thr Asp Glu Thr Val Ile
385                 390                 395                 400

GTT ATC AGA ACT CCA ACC AGT GAA GGT TTG GTT ACA ACC ACC ACT GAA      1248
Val Ile Arg Thr Pro Thr Ser Glu Gly Leu Val Thr Thr Thr Thr Glu
                405                 410                 415

CCA TGG ACT GGT ACT TTT ACT TCG ACT TCC ACT GAA ATG TCT ACT GTC      1296
Pro Trp Thr Gly Thr Phe Thr Ser Thr Ser Thr Glu Met Ser Thr Val
            420                 425                 430

ACT GGA ACC AAT GGC TTG CCA ACT GAT GAA ACT GTC ATT GTT GTC AAA      1344
Thr Gly Thr Asn Gly Leu Pro Thr Asp Glu Thr Val Ile Val Val Lys
            435                 440                 445

ACT CCA ACT ACT GCC ATC TCA TCC AGT TTG TCA TCA TCT TCA GGA          1392
Thr Pro Thr Thr Ala Ile Ser Ser Ser Leu Ser Ser Ser Ser Ser Gly
            450                 455                 460

CAA ATC ACC AGC TCT ATC ACG TCT TCG CGT CCA ATT ATT ACC CCA TTC      1440
Gln Ile Thr Ser Ser Ile Thr Ser Ser Arg Pro Ile Ile Thr Pro Phe
465                 470                 475                 480
```

-continued

```
TAT CCT AGC AAT GGA ACT TCT GTG ATT TCT TCC TCA GTA ATT TCT TCC        1488
Tyr Pro Ser Asn Gly Thr Ser Val Ile Ser Ser Ser Val Ile Ser Ser
                485                 490                 495

TCA GTC ACT TCT TCT CTA TTC ACT TCT TCT CCA GTC ATT TCT TCC TCA        1536
Ser Val Thr Ser Ser Leu Phe Thr Ser Ser Pro Val Ile Ser Ser Ser
            500                 505                 510

GTC ATT TCT TCT TCT ACA ACA ACC TCC ACT TCT ATA TTT TCT GAA TCA        1584
Val Ile Ser Ser Ser Thr Thr Thr Ser Thr Ser Ile Phe Ser Glu Ser
            515                 520                 525

TCT AAA TCA TCC GTC ATT CCA ACC AGT AGT TCC ACC TCT GGT TCT TCT        1632
Ser Lys Ser Ser Val Ile Pro Thr Ser Ser Ser Thr Ser Gly Ser Ser
    530                 535                 540

GAG AGC GAA ACG AGT TCA GCT GGT TCT GTC TCT TCT TCC TCT TTT ATC        1680
Glu Ser Glu Thr Ser Ser Ala Gly Ser Val Ser Ser Ser Ser Phe Ile
545                 550                 555                 560

TCT TCT GAA TCA TCA AAA TCT CCT ACA TAT TCT TCT TCA TCA TTA CCA        1728
Ser Ser Glu Ser Ser Lys Ser Pro Thr Tyr Ser Ser Ser Ser Leu Pro
                565                 570                 575

CTT GTT ACC AGT GCG ACA ACA AGC CAG GAA ACT GCT TCT TCA TTA CCA        1776
Leu Val Thr Ser Ala Thr Thr Ser Gln Glu Thr Ala Ser Ser Leu Pro
                580                 585                 590

CCT GCT ACC ACT ACA AAA ACG AGC GAA CAA ACC ACT TTG GTT ACC GTG        1824
Pro Ala Thr Thr Thr Lys Thr Ser Glu Gln Thr Thr Leu Val Thr Val
                595                 600                 605

ACA TCC TGC GAG TCT CAT GTG TGC ACT GAA TCC ATC TCC CCT GCG ATT        1872
Thr Ser Cys Glu Ser His Val Cys Thr Glu Ser Ile Ser Pro Ala Ile
        610                 615                 620

GTT TCC ACA GCT ACT GTT ACT GTT AGC GGC GTC ACA ACA GAG TAT ACC        1920
Val Ser Thr Ala Thr Val Thr Val Ser Gly Val Thr Thr Glu Tyr Thr
625                 630                 635                 640

ACA TGG TGC CCT ATT TCT ACT ACA GAG ACA ACA AAG CAA ACC AAA GGG        1968
Thr Trp Cys Pro Ile Ser Thr Thr Glu Thr Thr Lys Gln Thr Lys Gly
                645                 650                 655

ACA ACA GAG CAA ACC ACA GAA ACA ACA AAA CAA ACC ACG GTA GTT ACA        2016
Thr Thr Glu Gln Thr Thr Glu Thr Thr Lys Gln Thr Thr Val Val Thr
                660                 665                 670

ATT TCT TCT TGT GAA TCT GAC GTA TGC TCT AAG ACT GCT TCT CCA GCC        2064
Ile Ser Ser Cys Glu Ser Asp Val Cys Ser Lys Thr Ala Ser Pro Ala
            675                 680                 685

ATT GTA TCT ACA AGC ACT GCT ACT ATT AAC GGC GTT ACT ACA GAA TAC        2112
Ile Val Ser Thr Ser Thr Ala Thr Ile Asn Gly Val Thr Thr Glu Tyr
            690                 695                 700

ACA ACA TGG TGT CCT ATT TCC ACC ACA GAA TCG AGG CAA CAA ACA ACG        2160
Thr Thr Trp Cys Pro Ile Ser Thr Thr Glu Ser Arg Gln Gln Thr Thr
705                 710                 715                 720

CTA GTT ACT GTT ACT TCC TGC GAA TCT GGT GTG TGT TCC GAA ACT GCT        2208
Leu Val Thr Val Thr Ser Cys Glu Ser Gly Val Cys Ser Glu Thr Ala
                725                 730                 735

TCA CCT GCC ATT GTT TCG ACG GCC ACG GCT ACT GTG AAT GAT GTT GTT        2256
Ser Pro Ala Ile Val Ser Thr Ala Thr Ala Thr Val Asn Asp Val Val
                740                 745                 750

ACG GTC TAT CCT ACA TGG AGG CCA CAG ACT GCG AAT GAA GAG TCT GTC        2304
Thr Val Tyr Pro Thr Trp Arg Pro Gln Thr Ala Asn Glu Glu Ser Val
                755                 760                 765

AGC TCT AAA ATG AAC AGT GCT ACC GGT GAG ACA ACA ACC AAT ACT TTA        2352
Ser Ser Lys Met Asn Ser Ala Thr Gly Glu Thr Thr Thr Asn Thr Leu
        770                 775                 780

GCT GCT GAA ACG ACT ACC AAT ACT GTA GCT GCT GAG ACG ATT ACC AAT        2400
Ala Ala Glu Thr Thr Thr Asn Thr Val Ala Ala Glu Thr Ile Thr Asn
785                 790                 795                 800
```

```
ACT GGA GCT GCT GAG ACG AAA ACA GTA GTC ACC TCT TCG CTT TCA AGA      2448
Thr Gly Ala Ala Glu Thr Lys Thr Val Val Thr Ser Ser Leu Ser Arg
                805                 810                 815

TCT AAT CAC GCT GAA ACA CAG ACG GCT TCC GCG ACC GAT GTG ATT GGT      2496
Ser Asn His Ala Glu Thr Gln Thr Ala Ser Ala Thr Asp Val Ile Gly
                820                 825                 830

CAC AGC AGT AGT GTT GTT TCT GTA TCC GAA ACT GGC AAC ACC AAG AGT      2544
His Ser Ser Ser Val Val Ser Val Ser Glu Thr Gly Asn Thr Lys Ser
                835                 840                 845

CTA ACA AGT TCC GGG TTG AGT ACT ATG TCG CAA CAG CCT CGT AGC ACA      2592
Leu Thr Ser Ser Gly Leu Ser Thr Met Ser Gln Gln Pro Arg Ser Thr
        850                 855                 860

CCA GCA AGC AGC ATG GTA GGA TAT AGT ACA GCT TCT TTA GAA ATT TCA      2640
Pro Ala Ser Ser Met Val Gly Tyr Ser Thr Ala Ser Leu Glu Ile Ser
865                 870                 875                 880

ACG TAT GCT GGC AGT GCA ACA GCT TAC TGG CCG GTA GTG GTT TAA          2685
Thr Tyr Ala Gly Ser Ala Thr Ala Tyr Trp Pro Val Val Val
                    885                 890                 895
```

(2) INFORMATION FOR SEQ ID NO: 15:

(i) SEQUENCE CHARACTERISTICS:
        (A) LENGTH: 894 amino acids
        (B) TYPE: amino acid
        (D) TOPOLOGY: linear (ii) MOLECULE TYPE: protein (xi) SEQUENCE DESCRIPTION: SEQ ID NO: 15:

```
Met Thr Met Pro His Arg Tyr Met Phe Leu Ala Val Phe Thr Leu Leu
 1               5                  10                  15

Ala Leu Thr Ser Val Ala Ser Gly Ala Thr Glu Ala Cys Leu Pro Ala
             20                  25                  30

Gly Gln Arg Lys Ser Gly Met Asn Ile Asn Phe Tyr Gln Tyr Ser Leu
         35                  40                  45

Lys Asp Ser Ser Thr Tyr Ser Asn Ala Ala Tyr Met Ala Tyr Gly Tyr
     50                  55                  60

Ala Ser Lys Thr Lys Leu Gly Ser Val Gly Gly Gln Thr Asp Ile Ser
 65                  70                  75                  80

Ile Asp Tyr Asn Ile Pro Cys Val Ser Ser Ser Gly Thr Phe Pro Cys
                 85                  90                  95

Pro Gln Glu Asp Ser Tyr Gly Asn Trp Gly Cys Lys Gly Met Gly Ala
             100                 105                 110

Cys Ser Asn Ser Gln Gly Ile Ala Tyr Trp Ser Thr Asp Leu Phe Gly
         115                 120                 125

Phe Tyr Thr Thr Pro Thr Asn Val Thr Leu Glu Met Thr Gly Tyr Phe
     130                 135                 140

Leu Pro Pro Gln Thr Gly Ser Tyr Thr Phe Lys Phe Ala Thr Val Asp
145                 150                 155                 160

Asp Ser Ala Ile Leu Ser Val Gly Gly Ala Thr Ala Phe Asn Cys Cys
                 165                 170                 175

Ala Gln Gln Gln Pro Pro Ile Thr Ser Thr Asn Phe Thr Ile Asp Gly
             180                 185                 190

Ile Lys Pro Trp Gly Gly Ser Leu Pro Pro Asn Ile Glu Gly Thr Val
         195                 200                 205

Tyr Met Tyr Ala Gly Tyr Tyr Tyr Pro Met Lys Val Val Tyr Ser Asn
     210                 215                 220
```

```
Ala Val Ser Trp Gly Thr Leu Pro Ile Ser Val Thr Leu Pro Asp Gly
225                 230                 235                 240

Thr Thr Val Ser Asp Asp Phe Glu Gly Tyr Val Tyr Ser Phe Asp Asp
            245                 250                 255

Asp Leu Ser Gln Ser Asn Cys Thr Val Pro Asp Pro Ser Asn Tyr Ala
                260                 265                 270

Val Ser Thr Thr Thr Thr Thr Glu Pro Trp Thr Gly Thr Phe Thr
            275                 280                 285

Ser Thr Ser Thr Glu Met Thr Thr Val Thr Gly Thr Asn Gly Val Pro
290                 295                 300

Thr Asp Glu Thr Val Ile Val Ile Arg Thr Pro Thr Ser Glu Gly Leu
305                 310                 315                 320

Ile Ser Thr Thr Thr Glu Pro Trp Thr Gly Thr Phe Thr Ser Thr Ser
                325                 330                 335

Thr Glu Val Thr Thr Ile Thr Gly Thr Asn Gly Gln Pro Thr Asp Glu
                340                 345                 350

Thr Val Ile Val Ile Arg Thr Pro Thr Ser Glu Gly Leu Ile Ser Thr
                355                 360                 365

Thr Thr Glu Pro Trp Thr Gly Thr Phe Thr Ser Thr Ser Thr Glu Met
370                 375                 380

Thr Thr Val Thr Gly Thr Asn Gly Gln Pro Thr Asp Glu Thr Val Ile
385                 390                 395                 400

Val Ile Arg Thr Pro Thr Ser Glu Gly Leu Val Thr Thr Thr Thr Glu
                405                 410                 415

Pro Trp Thr Gly Thr Phe Thr Ser Thr Ser Thr Glu Met Ser Thr Val
                420                 425                 430

Thr Gly Thr Asn Gly Leu Pro Thr Asp Glu Thr Val Ile Val Val Lys
            435                 440                 445

Thr Pro Thr Thr Ala Ile Ser Ser Ser Leu Ser Ser Ser Ser Ser Gly
            450                 455                 460

Gln Ile Thr Ser Ser Ile Thr Ser Ser Arg Pro Ile Ile Thr Pro Phe
465                 470                 475                 480

Tyr Pro Ser Asn Gly Thr Ser Val Ile Ser Ser Ser Val Ile Ser Ser
                485                 490                 495

Ser Val Thr Ser Ser Leu Phe Thr Ser Ser Pro Val Ile Ser Ser Ser
            500                 505                 510

Val Ile Ser Ser Ser Thr Thr Thr Ser Thr Ser Ile Phe Ser Glu Ser
            515                 520                 525

Ser Lys Ser Ser Val Ile Pro Thr Ser Ser Ser Thr Ser Gly Ser Ser
530                 535                 540

Glu Ser Glu Thr Ser Ser Ala Gly Ser Val Ser Ser Ser Ser Phe Ile
545                 550                 555                 560

Ser Ser Glu Ser Ser Lys Ser Pro Thr Tyr Ser Ser Ser Ser Leu Pro
                565                 570                 575

Leu Val Thr Ser Ala Thr Thr Ser Gln Glu Thr Ala Ser Ser Leu Pro
            580                 585                 590

Pro Ala Thr Thr Thr Lys Thr Ser Glu Gln Thr Thr Leu Val Thr Val
            595                 600                 605

Thr Ser Cys Glu Ser His Val Cys Thr Glu Ser Ile Ser Pro Ala Ile
            610                 615                 620

Val Ser Thr Ala Thr Val Thr Val Ser Gly Val Thr Thr Glu Tyr Thr
625                 630                 635                 640

Thr Trp Cys Pro Ile Ser Thr Thr Glu Thr Thr Lys Gln Thr Lys Gly
```

```
                        645                 650                 655
Thr Thr Glu Gln Thr Thr Glu Thr Thr Lys Gln Thr Thr Val Val Thr
                    660                 665                 670
Ile Ser Ser Cys Glu Ser Asp Val Cys Ser Lys Thr Ala Ser Pro Ala
                675                 680                 685
Ile Val Ser Thr Ser Thr Ala Thr Ile Asn Gly Val Thr Thr Glu Tyr
            690                 695                 700
Thr Thr Trp Cys Pro Ile Ser Thr Thr Glu Ser Arg Gln Gln Thr Thr
705                 710                 715                 720
Leu Val Thr Val Thr Ser Cys Glu Ser Gly Val Cys Ser Glu Thr Ala
                725                 730                 735
Ser Pro Ala Ile Val Ser Thr Ala Thr Ala Thr Val Asn Asp Val Val
                740                 745                 750
Thr Val Tyr Pro Thr Trp Arg Pro Gln Thr Ala Asn Glu Glu Ser Val
            755                 760                 765
Ser Ser Lys Met Asn Ser Ala Thr Gly Glu Thr Thr Thr Asn Thr Leu
        770                 775                 780
Ala Ala Glu Thr Thr Thr Asn Thr Val Ala Ala Glu Thr Ile Thr Asn
785                 790                 795                 800
Thr Gly Ala Ala Glu Thr Lys Thr Val Val Thr Ser Ser Leu Ser Arg
                805                 810                 815
Ser Asn His Ala Glu Thr Gln Thr Ala Ser Ala Thr Asp Val Ile Gly
                820                 825                 830
His Ser Ser Ser Val Val Ser Val Ser Glu Thr Gly Asn Thr Lys Ser
            835                 840                 845
Leu Thr Ser Ser Gly Leu Ser Thr Met Ser Gln Gln Pro Arg Ser Thr
850                 855                 860
Pro Ala Ser Ser Met Val Gly Tyr Ser Thr Ala Ser Leu Glu Ile Ser
865                 870                 875                 880
Thr Tyr Ala Gly Ser Ala Thr Ala Tyr Trp Pro Val Val Val
                885                 890
```

(2) INFORMATION FOR SEQ ID NO: 16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: ChoB template coding strand (xi) SEQUENCE DESCRIPTION: SEQ ID NO: 16:

GCCCCCAGCC GCACCCTCG                                          19

(2) INFORMATION FOR SEQ ID NO: 17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: ChoB template non-coding strand (xi) SEQUENCE DESCRIPTION: SEQ ID NO: 17:

CGAGGGTGCG GCTGGGGGC                                                      19

(2) INFORMATION FOR SEQ ID NO: 18:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: cho01pcr primer (xi) SEQUENCE DESCRIPTION: SEQ ID NO: 18:

AGATCTGAAT TCGCGGCCGC CCCCAGCCGC ACCCTCG                                   37

(2) INFORMATION FOR SEQ ID NO: 19:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: cho02pcr primer (xi) SEQUENCE DESCRIPTION: SEQ ID NO: 19:

AGATCTAAGC TTTCAGCTAG CCTGGATGTC GGACGAGATG AT                             42

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: ChoB template coding strand (xi) SEQUENCE DESCRIPTION: SEQ ID NO: 20:

ATCATCTCGT CCGACATCCA G                                                   21

(2) INFORMATION FOR SEQ ID NO: 21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: ChoB template non-coding strand (xi) SEQUENCE DESCRIPTION: SEQ ID NO: 21:

CTGGATGTCG GACGAGATGA T                                                   21

(2) INFORMATION FOR SEQ ID NO: 22:

```
        (i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: mutagenesis primer ChoB (xi) SEQUENCE DESCRIPTION: SEQ ID NO: 22:

CGCGGCGACG GCACCGCCGT ATGCACTGGC GATGACGAGG GC                          42

(2) INFORMATION FOR SEQ ID NO: 23:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: ChoB template coding strand (xi) SEQUENCE DESCRIPTION: SEQ ID NO: 23:

GCCCTCGTCA TCGGCAGTGG ATACGGCGGT GCCGTCGCCG CG                          42

(2) INFORMATION FOR SEQ ID NO: 24:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: primer prt1

(xi) SEQUENCE DESCRIPTION: SEQ ID NO: 24:

AAGATCTATC GATCTTGTTA GCCGGTACA                                         29

(2) INFORMATION FOR SEQ ID NO: 25:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: proteinase template non-coding strand (xi) SEQUENCE DESCRIPTION: SEQ ID NO: 25:

GACTGTACCG GCTAACAAGA TCGATAGCCC TT                                     32

(2) INFORMATION FOR SEQ ID NO: 26:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)
```

(vii) IMMEDIATE SOURCE:
              (B) CLONE: proteinase template coding strand (xi) SEQUENCE DESCRIPTION: SEQ ID NO: 26:

GTCGGCGAAA TCCAAGCAAA GGCGGCT                                                27

(2) INFORMATION FOR SEQ ID NO: 27:

(i) SEQUENCE CHARACTERISTICS:
              (A) LENGTH: 39 base pairs
              (B) TYPE: nucleic acid
              (C) STRANDEDNESS: single
              (D) TOPOLOGY: linear (ii) MOLECULE TYPE: DNA (genomic)

(vii) IMMEDIATE SOURCE:
              (B) CLONE: prt2 primer (xi) SEQUENCE DESCRIPTION: SEQ ID NO: 27:

CCCAAGCTTC CCCCCGGCCG TTGCTTGGAT TTCGCCGAC                                   39

(2) INFORMATION FOR SEQ ID NO: 28:

(i) SEQUENCE CHARACTERISTICS:
              (A) LENGTH: 33 base pairs
              (B) TYPE: nucleic acid
              (C) STRANDEDNESS: single
              (D) TOPOLOGY: linear (ii) MOLECULE TYPE: DNA (genomic)

(vii) IMMEDIATE SOURCE:
              (B) CLONE: EGF1 primer (xi) SEQUENCE DESCRIPTION: SEQ ID NO: 28:

GGGGCGGCCG CGCTGGAGGA AAAGAAAGTT TGC                                         33

(2) INFORMATION FOR SEQ ID NO: 29:

(i) SEQUENCE CHARACTERISTICS:
              (A) LENGTH: 33 base pairs
              (B) TYPE: nucleic acid
              (C) STRANDEDNESS: single
              (D) TOPOLOGY: linear (ii) MOLECULE TYPE: DNA (genomic)

(vii) IMMEDIATE SOURCE:
              (B) CLONE: EGF receptor template non-coding strand (xi) SEQUENCE DESCRIPTION: SEQ ID NO: 29:

GCAAACTTTC TTTTCCTCCA GAGCCCGACT CGC                                         33

(2) INFORMATION FOR SEQ ID NO: 30:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (genomic)

(vii) IMMEDIATE SOURCE:
              (B) CLONE: EGF receptor template coding strand (xi) SEQUENCE DESCRIPTION: SEQ ID NO: 30:

AATGGGCCTA AGATCCCGTC CATCGCCACT                                             30

(2) INFORMATION FOR SEQ ID NO: 31:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: EGF2 primer (xi) SEQUENCE DESCRIPTION: SEQ ID NO: 31:

```
CCCCAAGCTT AAGGCTAGCG GACGGGATCT TAGGCCCATT                40
```

(2) INFORMATION FOR SEQ ID NO: 32:

(i) SEQUENCE CHARACTERISTICS:
        (A) LENGTH: 177 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: VhC - AGa1 linker with MycT and Hinge (xi) SEQUENCE DESCRIPTION: SEQ ID NO: 32:

```
GAATTCCAGG TCACCGTCTC CTCAGAACAA AAACTCATCT CAGAAGAGGA TCTGAATGAA    60
CCAAAGATTC CACAACCTCA ACCAAAGCCA CAACCTCAAC CACAACCACA ACCAAAACCT   120
CAACCAAAGC CAGAACCAGA ATCTACTTCC CCAAAGTCTC CAGCTAGCCT TAAGCTT      177
```

(2) INFORMATION FOR SEQ ID NO: 33:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: VhC - AGa1 linker with MycT (xi) SEQUENCE DESCRIPTION: SEQ ID NO: 33:

```
GAATTCCAGG TCACCGTCTC CTCAGAACAA AAACTCATCT CAGAAGAGGA TCTGAATGCT    60
AGC                                                                 63
```

(2) INFORMATION FOR SEQ ID NO: 34:

(i) SEQUENCE CHARACTERISTICS:
        (A) LENGTH: 144 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: VhC - AGa1 linker with Hinge (xi) SEQUENCE DESCRIPTION: SEQ ID NO: 34:

```
GAATTCCAGG TCACCGTCTC CTCAGAACCA AAGATTCCAC AACCTCAACC AAAGCCACAA    60
```

```
CCTCAACCAC AACCACAACC AAAACCTCAA CCAAAGCCAG AACCAGAATC TACTTCCCCA      120

AAGTCTCCAG CTAGCCTTAA GCTT                                           144

(2) INFORMATION FOR SEQ ID NO: 35:

(i) SEQUENCE CHARACTERISTICS:
        (A) LENGTH: 119 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: fragment in pUR4421 coding strand (xi) SEQUENCE DESCRIPTION: SEQ ID NO: 35:

AATTTAGCGG CCGCCCAGGT GAAACTGCTC GAGTAAGTGA CTAAGGTCAC CGTCTCCTCA      60

GAACAAAAAC TCATCTCAGA AGAGGATCTG AATTAATGAG AATTCATCAA ACGGTGATA      119

(2) INFORMATION FOR SEQ ID NO: 36:

(i) SEQUENCE CHARACTERISTICS:
        (A) LENGTH: 119 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: fragment in pUR4421 non-coding strand (xi) SEQUENCE DESCRIPTION: SEQ ID NO: 36:

AGCTTATCAC CGTTTGATGA ATTCTCATTA ATTCAGATCC TCTTCTGAGA TGAGTTTTTG      60

TTCTGAGGAG ACGGTGACCT TAGTCACTTA CTCGAGCAGT TTCACCTGGG CGGCCGCTA      119

(2) INFORMATION FOR SEQ ID NO: 37:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: Myc tail (xi) SEQUENCE DESCRIPTION: SEQ ID NO: 37:

Glu Gln Lys Leu Ile Ser Glu Glu Asp Leu Asn
1               5                   10

(2) INFORMATION FOR SEQ ID NO: 38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: BstEII-HindIII linker coding strand (xi) SEQUENCE DESCRIPTION: SEQ ID NO: 38:
```

```
GTCACCGTCT CCTCATAATG A                                             21

(2) INFORMATION FOR SEQ ID NO: 39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: BstEII HindIII linker non-coding strand (xi) SEQUENCE DESCRIPTION: SEQ ID NO: 39:

AGCTTCATTA TGAGGAGACG                                               20

(2) INFORMATION FOR SEQ ID NO: 40:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:         (B) CLONE: primer cho03pcr (xi) SEQUENCE DESCRIPTION: SEQ ID NO: 40:

CGGATCCAAG CTTGAGCCTG GATGTCGGAC GAGATGAT                           38
```

IMMOBILIZED PROTEINS WITH SPECIFIC BINDING CAPACITIES AND THEIR USE IN PROCESSES AND PRODUCTS

This is a continuation of application Ser. No. 08/492,114, filed on Nov. 1, 1995, which was abandoned upon the filing hereof and which is the national stage of PCT/EP94/00427, filed Feb. 10, 1994.

BACKGROUND OF THE INVENTION

The pharmaceutical, the fine chemicals and the food industry need a number of compounds that have to be isolated from complex mixtures such as extracts of animal or plant tissue, or fermentation broth. Often these isolation processes determine the price of the product.

Conventional isolation processes are not very specific and during the isolation processes the compound to be isolated is diluted considerably with the consequence that expensive steps for removing water or other solvents have to be applied.

For the isolation of some specific compounds affinity techniques are used. The advantage of these techniques is that the compounds bind very specifically to a certain ligand. However these ligands are quite often very expensive.

To avoid spillage of these expensive ligands they can be linked to an insoluble Support. However, often linking the ligand is also expensive and, moreover, the functionality of the ligand is often affected negatively by such procedure.

So a need exists for developing cheap processes for preparing highly effective immobilized ligands.

SUMMARY OF THE INVENTION

The invention provides a method for immobilizing a binding protein capable of binding to a specific compound, comprising the use of recombinant DNA techniques for producing said binding protein or a functional part thereof still having said specific binding capability, said protein or said part thereof being linked to the outside of a host cell, whereby said binding protein or said part thereof is localized in the cell wall or at the exterior of the cell wall by allowing the host cell to produce and secrete a chimeric protein in which said binding protein or said functional part thereof is bound with its C-terminus to the N-terminus of an anchoring part of an anchoring protein capable of anchoring in the cell wall of the host cell, which anchoring part is derivable from the C-terminal part of said anchoring protein.

Preferably, the host is selected from Gram-positive bacteria and fungi, which have a cell wall at the outside of the host cell, in contrast to Gram-negative bacteria and cells of higher eukaryotes such as animal cells and plant cells, which have a membrane at the outside of their cells. Suitable Gram-positive bacteria comprise lactic acid bacteria and bacteria belonging to the genera Bacillus and Streptomyces. Suitable fungi comprise yeasts belonging to the genera Candida, Debaryomyces, Hansenula, Kluyveromyces, Pichia and Saccharomyces, and moulds belonging to the genera Aspergillus, Penicillium and Rhizopus. In this specification the group of fungi comprises the group of yeasts and the group of moulds, which are also known as lower eukaryotes. In contrast to the cells in plants and animals, the group of bacteria and lower eukaryotes are also indicated in this specification as microorganisms. The invention also provides a recombinant polynucleotide capable of being used in a method as described above, such polynucleotide comprising (i) a structural gene encoding a binding protein or a functional part thereof still having the specific binding capability, and (ii) at least part of a gene encoding an anchoring protein capable of anchoring in the cell wall of a Gram-positive bacterium or a fungus, said part of a gene encoding at least the anchoring part of said anchoring protein, which anchoring part is derivable from the C-terminal part of said anchoring protein. The anchoring protein can be selected from α-agglutinin, a-agglutinin FLO1, the Major Cell Wall Protein of a lower eukaryote, and proteinase of lactic acid bacteria. Preferably, such polynucleotide further comprises a nucleotide sequence encoding a signal peptide ensuring secretion of the expression product of the polynucleotide, which signal peptide can be derived from a protein selected from the α-mating factor of yeast, α-agglutinin of yeast, invertase of Saccharomyces, insulinase of Kluyveromyces, α-amylase of Bacillus, and proteinase of lactic acid bacteria. The polynucleotide can be operably linked to a promoter, which is preferably an inducible promoter.

The invention further provides a recombinant vector comprising a polynucleotide according to the invention, a chimeric protein encoded by a polynucleotide according to the invention, and a host cell having a cell wall at the outside of its cell and containing at least one polynucleotide according to the invention. Preferably at least one polynucleotide is integrated in the chromosome of the host cell. Another embodiment of this part of the invention is a host cell having a chimeric protein according to the invention immobilized in its cell wall and having the binding protein part of the chimeric protein localized in the cell wall or at the exterior of the cell wall.

Another embodiment of the invention is a process for carrying out an isolation process by using an immobilized binding protein or functional part thereof still capable of binding to a specific compound, wherein a medium containing said specific compound is contacted with a host cell according to the invention under conditions whereby a complex between said specific compound and said immobilized binding protein is formed, separating said complex from the medium originally containing said specific compound and, optionally, releasing said specific compound from said binding protein or functional part thereof.

BRIEF DESCRIPTION OF THE FIGURES

The file of this patent contains at least one drawing executed in color. Copies of this patent with color drawings will be provided by the Patent and Trademark Office upon request and payment of the necessary fee.

In FIG. 5 the composition of plasmid pUR2743.4 is indicated. Its preparation is described in Example 2. It contains the 714 bp PstI-XhoI fragment given in SEQ ID NO: 12, which fragment encodes an scFv-TRAS fragment of anti-traseolide® antibody 02/01/01.

In FIG. 6 the composition of plasmid pUR4178 is indicated. Its preparation is indicated in Example 2. It contains the above mentioned 714 bp PstI-XhoI fragment given in SEQ ID NO: 12. This plasmid is suitable for the expression of a fusion protein between scFv-TRAS and αAGG preceded by the invertase signal sequence (SUC2).

In FIG. 7 the composition of plasmid pUR4179 is indicated. Its preparation is indicated in Example 2. It contains the above mentioned 714 bp PstI-XhoI fragment given in SEQ ID NO: 12. This plasmid is suitable for the expression of a fusion protein between scFv-TRAS and αAGG preceded by the prepro-α-mating factor signal signal sequence.

In FIG. 18 the composition of plasmids pUR4482 and 4483 is indicated. Their preparation is described in Example 9. Plasmid pUR4482 is a yeast episomal expression plasmid for expression of a fusion protein with the invertase signal sequence, the CH$_V$09 variable region, the Myc-tail, and the "X-P-X-P" Hinge region of a camel antibody, and the α-agglutinin cell wall anchor region. Plasmid pUR4483 differs from pUR4482 in that it does not contain the "X-P-X-P" Hinge region.

In FIG. 19 immunofluorescent labelling (anti-Myc antibody) of SU10 cells in the exponential phase (OD$_{530}$= 0.5) expressing the genes of camel antibodies present on plasmids pUR4424, pUR4482 and pUR4483 is shown.

Ph=phase contrast, Fl=fluorescence.

In FIG. 20 immunofluorescent labelling (anti-human IgG antibody) of SU10 cells in the exponential phase (OD$_{530}$= 0.5) expressing the genes of camel antibodies present on plasmids pUR4424, pUR4482 and pUR4483 is shown.

Ph=phase contrast, Fl=fluorescence.

Figure 15:
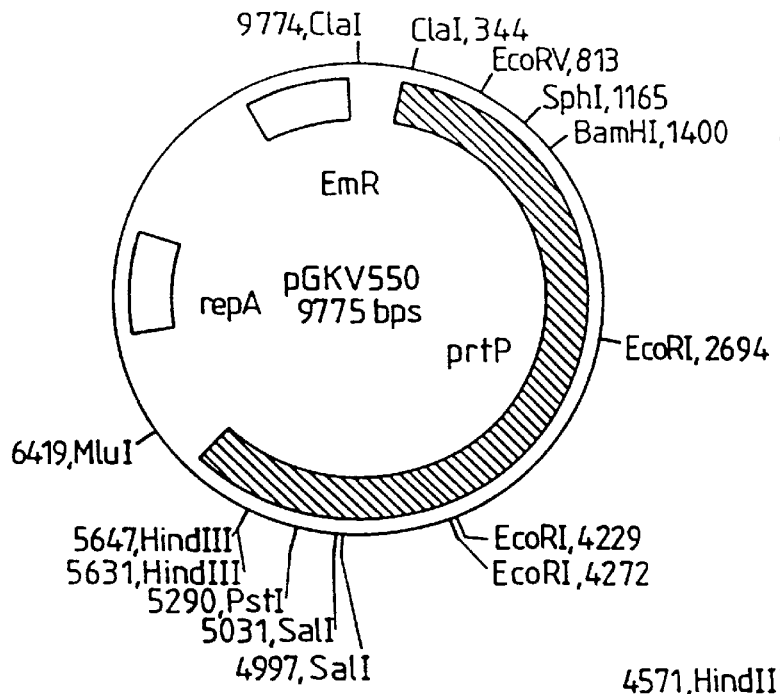
In FIG. 15 the composition of the published plasmid pGKV550 is indicated. It is described in Example 7 and contains the complete cell wall proteinase operon of Lactococcus lactis subsp. cremoris Wg2, including the promoter, the ribosome binding site and the prtP gene.

| Abbreviations used in the Figures: | |
|---|---|
| α-gal: | gene encoding guar α-galactosidase |
| AG-alpha-1/AGα1: | gene expressing α-agglutinin from S. cerevisiae |
| AGα1 cds/α-AGG: | coding sequence of α-agglutinin |
| Amp/amp r: | β-lactamase resistance gene |
| CH$_V$09: | camel heavy chain variable 09 fragment |
| EmR: | erythromycin resistance gene |
| f1: | phage f1 replication sequence |
| FLO1/FLO (C-part): | C-terminal part of FLO1 coding sequence of flocculation protein |
| Hinge: | Camel "X-P-X-P" Hinge region, see Example 9 |
| LEU2: | LEU2 gene |
| LEU2d/Leu2d: | truncated LEU2 gene |
| Leu 2d cs: | coding sequence LEU2d gene |
| MycT: | camel Myc-tail |
| Ori MB1: | origin of replication MB1 derived from E. coli plasmid |
| Pgal7/pGAL7: | GAL7 promoter |
| Tpgk: | terminator of the phosphoglyceratekinase gene |
| ppα-MF/MFα1ss: | prepro-part of α-mating factor (= signal sequence) |
| repA: | gene encoding the repA protein required for replication (FIG. 15/16). |
| ScFv (Vh-Vl): | single chain antibody fragment containing V$_H$ and V$_L$ chains |
| ss: | signal sequence |
| SUC2: | invertase signal sequence |
| 2u/2 micron: | 2 μm sequence |

DETAILED DESCRIPTION OF THE INVENTION

The present invention relates to the isolation of valuable compounds from complex mixtures by making use of immobilized ligands. The immobilized ligands can be proteins obtainable via genetic engineering and can consist of two parts, namely both an anchoring protein or functional part thereof and a binding protein or functional part thereof.

The anchoring protein sticks into cell walls of microorganisms, preferably lower eukaryotes, e.g. yeasts and moulds. Often this type of proteins has a long C-terminal part that anchors it in the cell wall. These C-terminal parts have very special amino acid sequences. A typical example is anchoring via C-terminal sequences of proteins enriched in proline, see Kok (1990).

The C-terminal part of these anchoring proteins can contain a substantial number of potential serine and threonine glycosylation sites. O-glycosylation of these sites gives a rod-like conformation to the C-terminal part of these proteins.

In the case of anchored manno-proteins they seem to be linked to the glucan in the cell wall of lower eukaryotes, as they cannot be extracted from the cell wall with sodium dodecyl sulphate (SDS), but can be liberated by glucanase treatment, see our co-pending patent application WO-94/01567 (UNILEVER) published Jan. 20, 1994 and Schreuder c.s. (1993), both being published after the claimed priority date. Another mechanism to anchor proteins at the outer side of a cell is to make use of the property that a protein containing a glycosyl-phosphatidyl-inositol (GPI) group anchors via this GPI group to the cell surface, see Conzelmann c.s. (1990).

The binding protein is so called, because it ligates or binds to the specific compound to be isolated. If the N-terminal part of the anchoring protein is sufficiently capable of binding to a specific compound, the anchoring protein itself can be used in a process for isolating that specific compound. Suitable examples of a binding protein comprise an antibody, an antibody fragment, a combination of antibody fragments, a receptor protein, an inactivated enzyme still capable of binding the corresponding substrate, and a peptide obtained via Applied Molecular Evolution, see Lewin (1990), as well as a part of any of these proteinaceous substances still capable of binding to the specific compound to be isolated. All these binding proteins are characterized by specific recognition of the compounds or group of related compounds to be isolated. The binding rate and release rate, and therefore the binding constant between the specific compound to be isolated and the binding protein, can be regulated either by changing the composition of the liquid extract in which the compound is present or, preferably, by changing the binding protein by protein engineering.

The gene coding for the chimeric protein comprising both the binding protein and the anchoring protein (or functional parts thereof) can be placed under control of a constitutive, inducible or derepressible promoter and will generally be preceded by a DNA fragment encoding a signal sequence ensuring efficient secretion of the chimeric protein. Upon secretion the chimeric protein will be anchored in the cell wall of the microorganisms, thereby covering the surface of the microorganisms with the chimeric protein. These microorganisms can be obtained in normal fermentation processes and their isolation is a cheap process, when physical separation processes are used, e.g. centrifugation or membrane filtration.

After washing, the isolated microorganisms can be added to liquid extracts containing the valuable specific compound or compounds. After some time the equilibrium between the bound and free specific compound(s) will be reached and the microorganisms to which the specific compound or group of related compounds is bound can be separated from the extract by simple physical techniques.

Alternatively, the microorganisms covered with ligands can be brought on a support material and subsequently this coated support material can be used in a column. The liquid extract containing the specific compound or compounds of interest can be added to the column and afterwards the compound(s) can be released from the ligand by changing the composition of the eluting liquid or the temperature or both. A skilled person will recognize that in addition to these two possibilities other modifications can be used for effecting the binding of the specific compound and the ligand, their subsequent isolation and/or the release of the specific compound(s). In particular the invention relates to chimeric proteins that are bound to the cell wall of lower eukaryotes. Suitable lower eukaryotes comprise yeasts, e.g. Candida, Debaryomyces, Hansenula, Kluyveromyces, Pichia and Saccharomyces, and moulds e.g. Aspergillus, Penicillium and Rhizopus. For some applications prokaryotes are also applicable, especially Gram-positive bacteria, examples of which include lactic acid bacteria, and bacteria belonging to the genera Bacillus and Streptomyces.

For lower eukaryotes the present invention provides genes encoding chimeric proteins consisting of:

a. a DNA sequence encoding a signal sequence functional in a lower eukaryotic host, e.g. derived from a yeast protein including the α-mating factor, invertase, α-agglutinin, inulinase or derived from a mould protein e.g. xylanase;

b. a structural gene encoding a C-terminal part of a cell wall protein preceded by a structural gene encoding a protein, that is capable of binding to the specific compound or group of compounds of interest, examples of which include an antibody, a single chain antibody fragment (scFv; see Bird and Webb Walker (1991), a variable region of the heavy chain ($V_H$) or a variable region of the light chain ($V_L$) of an antibody or that part of such variable region still containing one to three of the complementarity determining regions (CDRs), an agonist-recognizing part of a receptor protein or a part thereof still capable of binding the agonist, a catalytically inactivated enzyme, or a fragment of such enzyme still containing a substrate binding site of the enzyme, specific lipid binding proteins or parts of these proteins still containing the lipid binding site(s), see Ossendorp (1992), and a peptide that has been obtained via Applied Molecular Evolution, see Lewin (1990).

All expression products of these genes are characterized in that they consists of a signal sequence and both a protein part, that is capable of binding to the compound(s) to be isolated, and a C-terminus of a typically cell wall bound protein, examples of the latter including α-agglutinin, see Lipke c.s. (1989), a-agglutinin, see Roy c.s. (1991), FLO1 (see Example 5 and SEQ ID NO: 14) and the Major Cell Wall Protein of lower eukaryotes, which C-terminus is capable of anchoring the expression product in the cell wall of the lower eukaryote host organism.

The expression of these genes encoding chimeric proteins can be under control of a constitutive promoter, but an inducible promoter is preferred, suitable examples of which include the GAL7 promoter from Saccharomyces, the inulinase promoter from Kluyveromyces, the methanol-oxidase promoter from Hansenula, and the xylanase promoter of Aspergillus. Preferably the constructs are made in such a way that the new genetic information is integrated in a stable way in the chromosome of the host cell, see e.g. WO-91/00920 (UNILEVER).

The lower eukaryotes transformed with the above mentioned genes can be grown in normal fermentation, continuous fermentation, or fed batch fermentation processes. The selection of a suitable process for growing the microorganism will depend on the construction of the gene and the promoter used, and on the desired purity of the cells after the physical separation procedure(s).

For bacteria the present invention deals with genes encoding chimeric proteins consisting of:
   a. a DNA sequence encoding, a signal sequence functional in the specific bacterium, e.g. derived from a Bacillus α-amylase, a *Bacillus subtilis* subtilisin, or a *Lactococcus lactis* subsp. *cremoris* proteinase;
   b. a structural gene encoding a C-terminal part of a cell wall protein preceded by a structural gene encoding a protein capable of binding to the specific compound or group of compounds of interest, examples of which are given above for a lower eukaryote.

All expression products of these genes are characterized in that they consist of a signal sequence and both a protein part, that is capable of binding to the specific compound or specific group of compounds to be isolated, and a C-terminus of a typically cell wall-bound protein such as the proteinase of *Lactococcus lactis* subsp. *cremoris* strain Wg2, see Kok c.s. (1988) and Kok (1990), the C-terminus of which is capable of anchoring the expression product in the cell wall of the host bacterium.

The invention is illustrated with the following Examples without being limited thereto. First the endonuclease restriction sites mentioned in the Examples are given.

| BstEII | G GTNACC<br>CCANTG G | ClaI    | AT CGAT<br>TAGC TA | EagI | C GGCCG<br>GCCGG C |
|--------|----------------------|---------|--------------------|------|--------------------|
| EcoRI  | G AATTC<br>CTTAA G   | HindIII | A AGCTT<br>TTCGA A | NheI | G CTAGC<br>CGATC G |
| NotI   | GC GGCCGC<br>CGCCGG CG | NruI  | TCG CGA<br>AGC GCT | PstI | CTGCA G<br>G ACGTC |
| SacI   | GAGCT C<br>C TCGAG   | SalI    | G TCGAC<br>CAGCT G | XhoI | C TCGAG<br>GAGCT C |

EXAMPLE 1

Construction of a Gene Encoding a Chimeric Protein That Will Be Anchored in the Cell Wall of a Lower Eukaryote and is Able to Bind with High Specificity Lysozyme From a Complex Mixture Lysozyme is an anti-microbial enzyme with a number of applications in the pharmaceutical and food industries. Several sources of lysozyme are known, e.g. egg yolk or a fermentation broth containing a microorganism producing lysozyme.

Monoclonal antibodies have been raised against lysozyme, see Ward c.s. (1989), and the mRNA's encoding the light and heavy chains of such antibodies have been isolated from the hybridoma cells and used as template for the synthesis of cDNA using reverse transcriptase. Starting from the plasmids as described by Ward c.s. (1989), we constructed a pEMBL-derived plasmid, designated pUR4122, in which the multiple cloning site of the pEMBL-vector, ranging from the EcoRI to the HindIII site, was replaced by a 231 bp DNA fragment, whose nucleotide sequence is given in SEQ ID NO: 1 and has an EcoRI site (GAATTC) at nucleotides 1–6, a PstI site (CTGCAG) at nucleotides 105–110, a BstEII site (GGTCACC) at nucleotides 122–128, a XhoI site (CTCGAG) at nucleotides 207–212, and a HindIII site (AAGCTT) at nucleotides 226–231.

Construction of pUR4122

Figure 1:
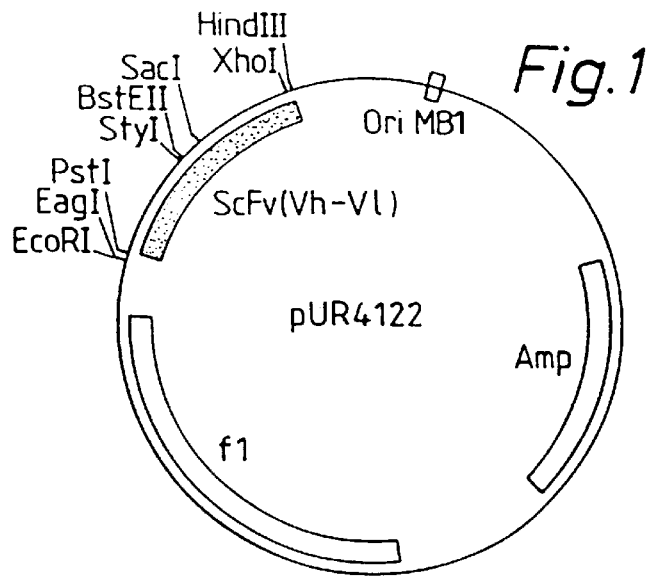
In FIG. 1 the composition of pEMBL9-derived plasmid pUR4122 is indicated, the preparation of which is described in Example 1.

Plasmid pEMBL9, see Dente c.s. (1983), was digested with EcoRI and HindIII and the resulting large fragment was ligated with the double stranded synthetic DNA fragment given in SEQ ID NO: 1. For the successive ligation of DNA fragments, which finally form the coding sequence of a single chain antibody fragment for lysozyme, the following elements were combined in the 231 bp DNA fragment (SEQ ID NO: 1) inserted into the pEMBL-9 vector: the 3' part of the GAL7 promoter, the invertase signal sequence (SUC2), a PstI restriction site, a BstEII restriction site, a sequence encoding the (GGGGS)×3 peptide linker connecting the $V_H$ and $V_L$ fragments, a SacI restriction site, a XhoI restriction site and a HindIII restriction site, resulting in plasmid pUR4119. To obtain the in frame fusion between $V_H$ and the GGGGS-linker plasmid pSW1-VHD1.3-VKD1.3-TAG1, see Ward c.s. (1989), was digested with PstI and BstEII and a DNA fragment of 0.35 kbp was ligated in the correspondingly digested pUR4119 resulting in plasmid pUR4119A. Subsequently the plasmid pSW1-VHD1.3-VKD1.3-TAC1 was digested with SacI and XhoI and this fragment containing the coding part of $V_L$ was finally ligated into the SacI/XhoI sites of pUR4119A, resulting in plasmid pUR4122 (see FIG. 1).

Figure 4A:
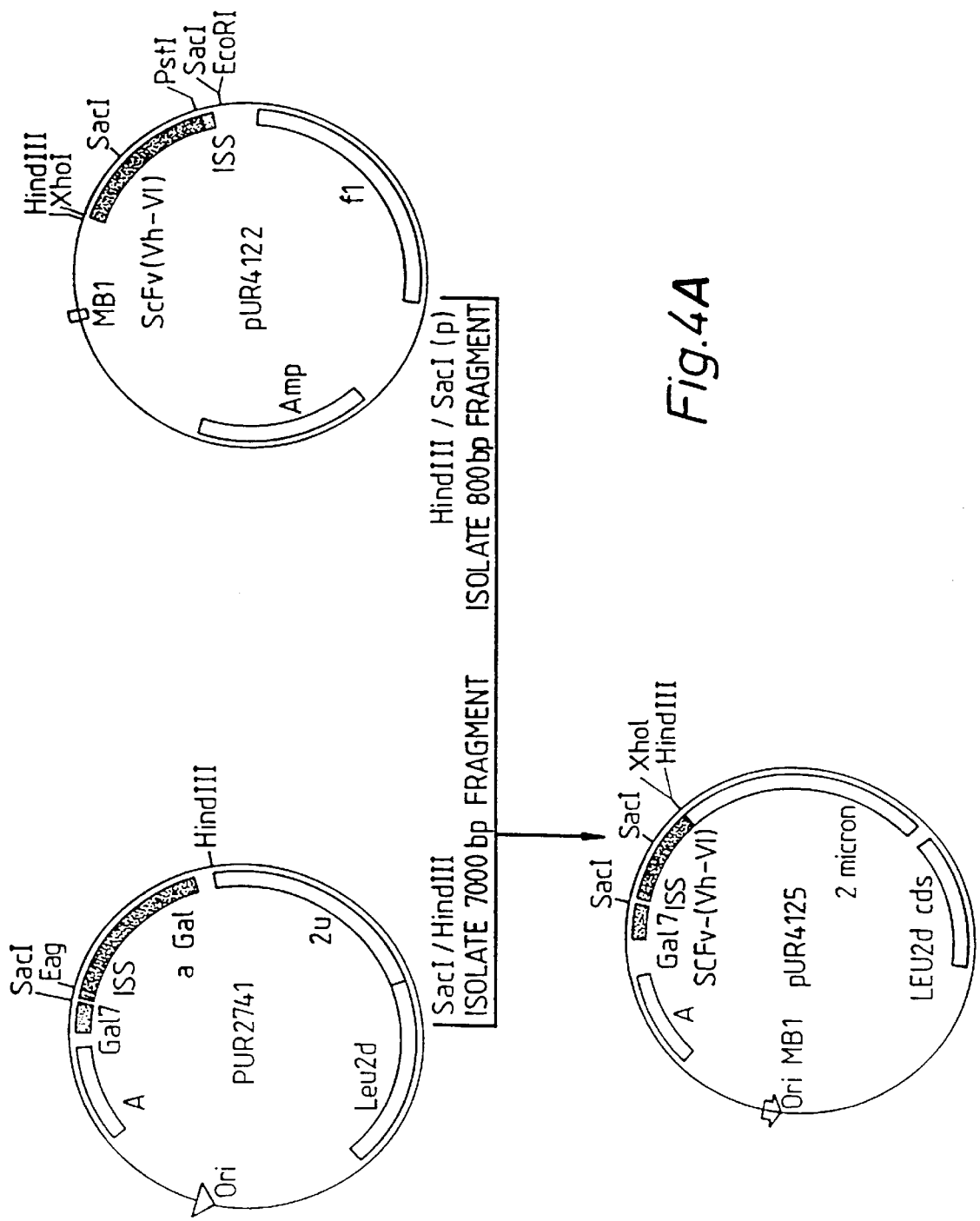
In FIGS. 4A–4C the preparation of plasmid pUR4174 starting from plasmids pUR2741, pUR2968 and pUR4122 is indicated, as well as the preparation of plasmid pUR4175 starting from plasmids pSY16, pUR2968 and pUR4122. These preparations are described in Example 1.
Figure 4B:
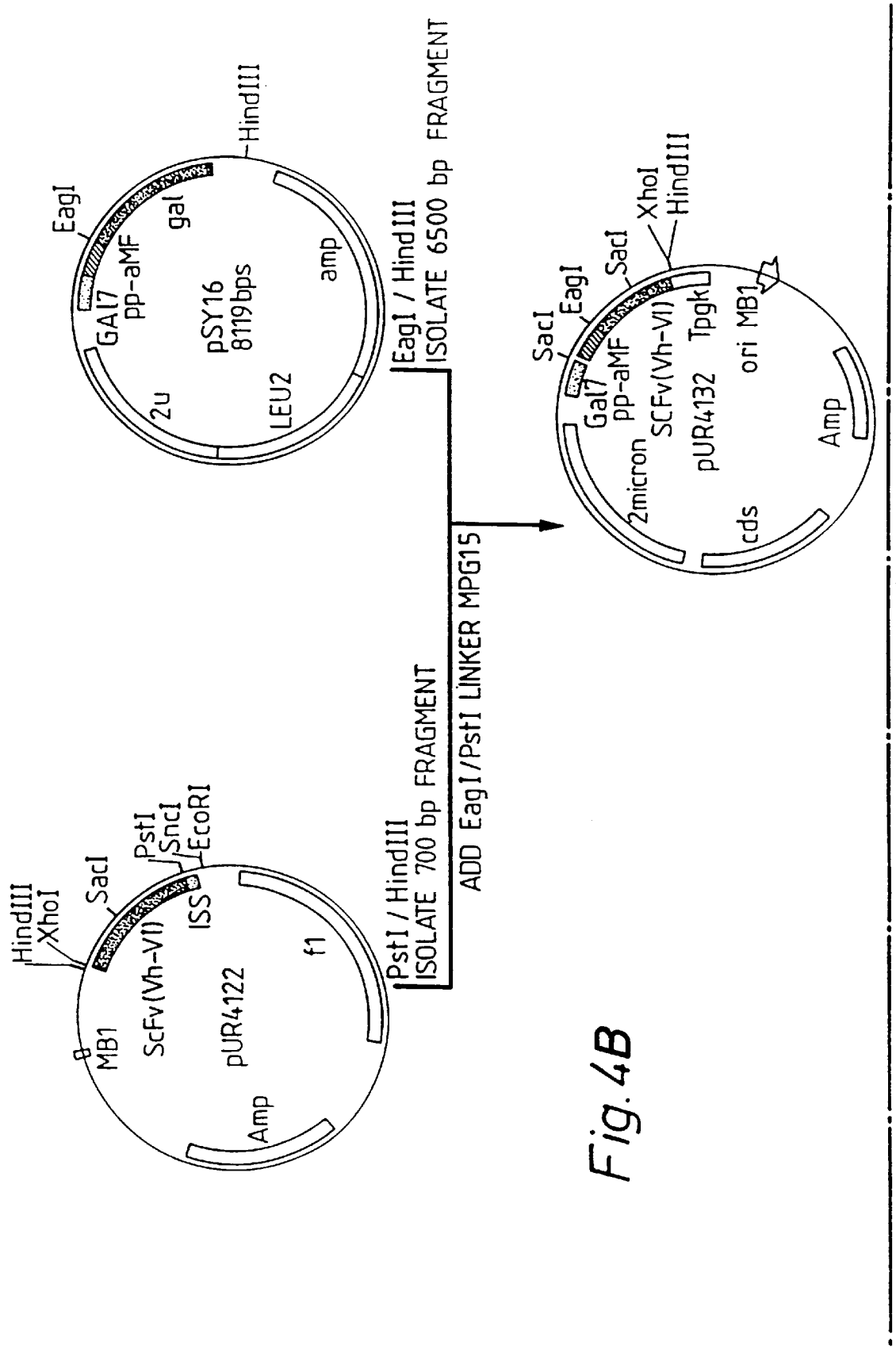
Figure 4C:
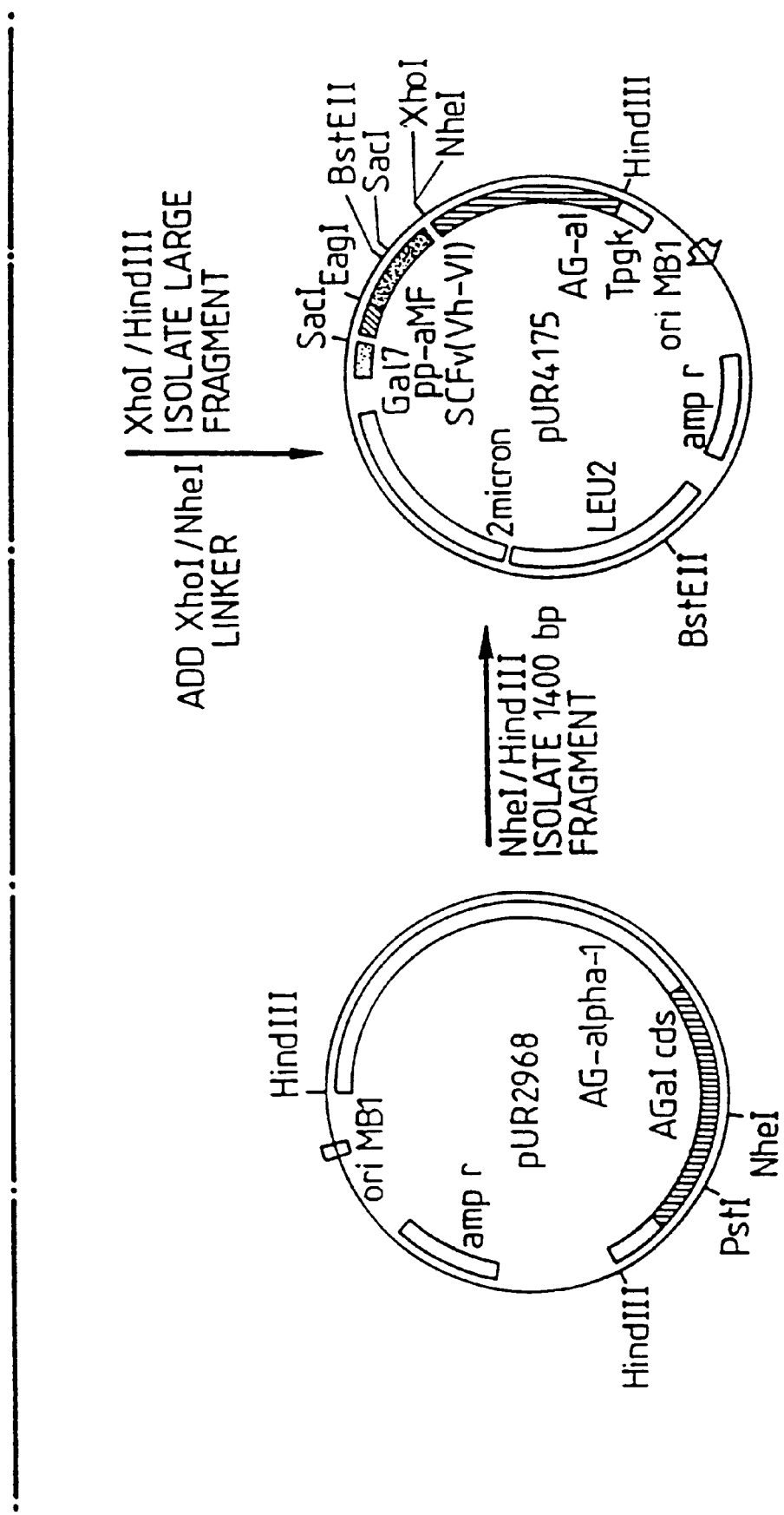

Construction of pUR4174 see FIG. 4

Figure 2:
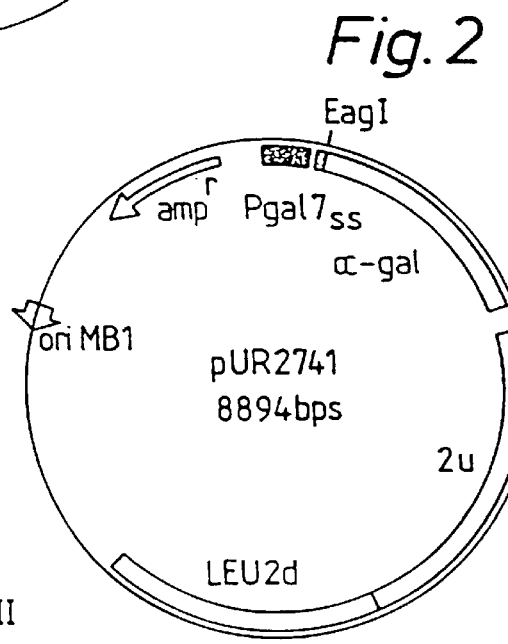
In FIG. 2 the composition of plasmid pUR2741 is indicated, which is a derivative of published plasmid pUR2740, see Example 1.

To obtain *S. cerevisiae* episomal expression plasmids containing DNA encoding a cell wall anchor derived from the C-terminal part of α-agglutinin, plasmid pUR2741 (see FIG. 2) was selected as starting vector. Basically, this plasmid is a derivative of pUR2740, which is a derivative of plasmid pUR2730 as described in WO-91/19782 (UNILEVER) and by Verbakel (1991). The preparation of pUR2730 is clearly described in Example 9 of EP-A1-0255153 (UNILEVER). Plasmid pUR2741 differs from plasmid pUR2740 in that the EagI restriction site within the remaining part of the already inactive tet resistance gene was deleted through NruI/SalI digestion. The SalI site was filled in prior to religation.

After digesting pUR4122 with SacI (partially) and HindIII, the approximately 800 bp fragment was isolated and cloned into the pUR2741 vector fragment, which was obtained after digestion of pUR2741 with the same enzymes. The resulting plasmid was named pUR4125.

Figure 3:
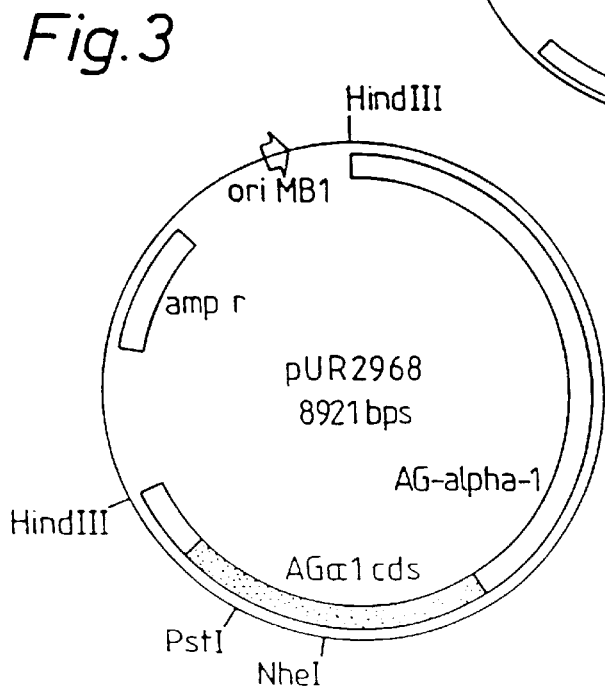
In FIG. 3 the composition of pEMBL9-derived plasmid pUR2968 is indicated. Its preparation is described in Example 1.

A plasmid named pUR2968 (see FIG. 3) was made by (1) digesting with HindIII the Aga1-containing plasmid pLα21 published by Lipke c.s. (1989), (2) isolating an about 6.1 kbp fragment and (3) ligating that fragment with HindIII-treated pEMBL9, so that the 6.1 kbp fragment was introduced into the HindIII site present in the multiple cloning site of the pEMBL9 vector.

Plasmid pUR4125 was digested with XhoI and HindIII and the about 8 kbp fragment was ligated with the approximately 1.4 kbp NheI-HindIII fragment of pUR2968, using XhoI/NheI adapters having the following sequence:

```
     XhoI                     NheI
5'-TC GAG ATC AAA GGC GGA TCT G    -3' =
                                        SEQ ID NO: 2
3'-      C TAG TTT CCG CCT AGA CGATC-5' =
                                        SEQ ID NO: 3.
```

The plasmid resulting from the ligation of the appropriate parts of plasmids pUR2968, pUR4125 and XhoI/NheI adapters, was designated pUR4174 and encodes a chimeric fusion protein at the amino terminus consisting of the invertase signal (pre) peptide, followed by the scFv-LYS polypeptide and, finally, the C-terminal part of α-agglutinin (see FIG. 4).

Construction of pUR4175. see FIG. 4

Upon digesting pUR4122 (see above) with PstI and HindIII, the approximately 700 bp fragment was isolated and ligated into a vector fragment of plasmid pSY16, see Harmsen c.s. (1993), which was digested with EagI and HindIII and using EagI-PstI adapters, having the following sequence:

```
  EagI                  PstI
5'-G GCC GCC CAG GTG CAG CTG CA-3' = SEQ ID NO: 4
3'-       CGG GTC CAC GTC G      -5' = SEQ ID NO: 5
```

The resulting plasmid, named pUR4132, was digested with XhoI and HindIII and ligated with the approximately 1.4 kbp NheI-HindIII fragment of pUR2968 (see above), using XhoI/NheI adapters as described above, resulting in pUR4175 (see FIG. 4). This plasmid contains a gene encoding a chimeric protein consisting of the α-mating factor prepro-peptide, followed by the scFv-LYS polypeptide and, finally, the C-terminal part of α-agglutinin.

EXAMPLE 2

Construction of Genes Encoding a Series of Homologous Chimeric Proteins That Will Be Anchored in the Cell Wall of a Lower Eukaryote and are Able to Bind with High Specificities the Musk Fragrance Traseolide® From a Complex Mixture The isolation of RNA from the hybridoma cell lines, the preparation of cDNA and amplification of gene fragments encoding the variable regions of antibodies by PCR was performed according to standard procedures known from the literature, see e.g. Orlandi c.s. (1989). For the PCR amplification different oligonucleotide primers have been used.

For the heavy chain fragment:

```
A:  AGG TSM ARC TGC AGS AGT CWG G = SEQ ID NO: 6
              PstI
``` in which S is C or G, M is A or C, R is A or G, and W is A or T, and

For the light chain fragment (Kappa):

```
C:  GAC ATT GAG CTC ACC CAG TCT CCA = SEQ ID NO: 8,
            SacI
``` and

```
D:  GTT TGA TCT CGA GCT TGG TCC C = SEQ ID NO: 9.
            XhoI
```

Construction of pUR4143

To simplify future construction work an EagI restriction site was introduced in pUR4122 (see above), at the junction between the invertase signal sequence and the scFv-LYS. This was achieved by replacing the about 110 bp EcoRI-PstI fragment within the synthetic fragment given in SEQ ID NO: 1 by synthetic adapters with the following sequence:

```
EcoRI                 PstI
AATTCGGCCGTTCAGGTGCAGCTGCA =    SEQ ID NO: 10
    GCCGGCAAGTCCACGTCG =        SEQ ID NO: 11.
```

The resulting plasmid was designated pUR4122.1: a construction vector for single chain Fv assembly in frame behind an EagI site for expression behind either the prepro-α-mating factor sequence or the SUC2 invertase signal sequence.

After digesting the heavy chain PCR fragment with PstI and BstEII, two fragments were obtained: a PstI fragment of about 230 bp and a PstI/BstEII fragment of about 110 bp. The latter fragment was cloned into vector pUR4122.1, which was digested with PstI and BstEII. The newly obtained plasmid (pUR4122.2) was digested with SacI and XhoI, after which the light chain PCR fragment (digested with the same restriction enzymes) was cloned into the vector, resulting in pUR4122.3. This plasmid was digested with PstI, after which the above described about 230 bp PstI fragment was cloned into the plasmid vector, resulting in a plasmid called pUR4143. Two orientations are possible, but selection can be made by restriction analysis, as usual. Instead of the scFv-LYS gene originally present in pUR4122, this new plasmid pUR4143 contains a gene encoding, an scFv-TRAS fragment of anti-traseolide antibody 02/01/01 (for the nucleotide sequence of the 714 bp PstI-XhoI fragment see SEQ ID NO: 12).

Construction of pUR4178 and pUR4179.

After digesting pUR4143, with EagI and HindIII, an about 715 bp fragment can be isolated. Subsequentely, this fragment can be cloned into the vector backbone fragments of pUR2741 and pUR4175, that were digested with the same restriction enzymes. In the case of pUR2741, this resulted in plasmid pUR2743.4 (see FIG. 5). This plasmid can subsequently be cleaved with XhoI and HindIII and ligated with the about 8 kbp XhoI-HindIII fragment of pUR4174, resulting in pUR4178 (see FIG. 6).

In the situation where pUR4175 was used as a starting vector, the resulting plasmid was designated pUR4179 (see FIG. 7).

Both plasmids, pUR4178 and pUR4179 were introduced into S. cerevisiae.

```
B:  TGA GGA GAC GGT GAC CGT GGT CCC TTG GCC CC = SEQ ID NO: 7.
              BstEII
```

EXAMPLE 3

The Modification of the Binding Parts of the Chimeric Protein That Can Bind Traseolide® in Order to Improve the Binding or Release of Traseolide® Under Certain Conditions Modification of binding properties of antibodies during the immune response is a well known immunological phenomenon originating from the fine tuning of complementarity determining sequences in the antibody's binding region to the antigen's molecular properties. This phenomenon can be mimicked in vitro by adjusting the antigen binding regions of antibody fragments based on molecular models of these regions in contact with the antigen.

One such example consists of protein engineering the antimusk antibody M02/01/01 to a stronger binding variant M020501i.

First, a molecular model of M02/01/01 variable fragment (Fv) was constructed by homology modelling, using the coordinates of the anti-lysozyme antibody HYHEL-10 as a template (Brookhaven Protein Data Bank entry: 3HFM). This model was refined using Molecular Mechanics and Molecular Dynamics methods from within the Biosym program DISCOVER, on a Silicon Graphics 4D240 workstation.

Figure 8:
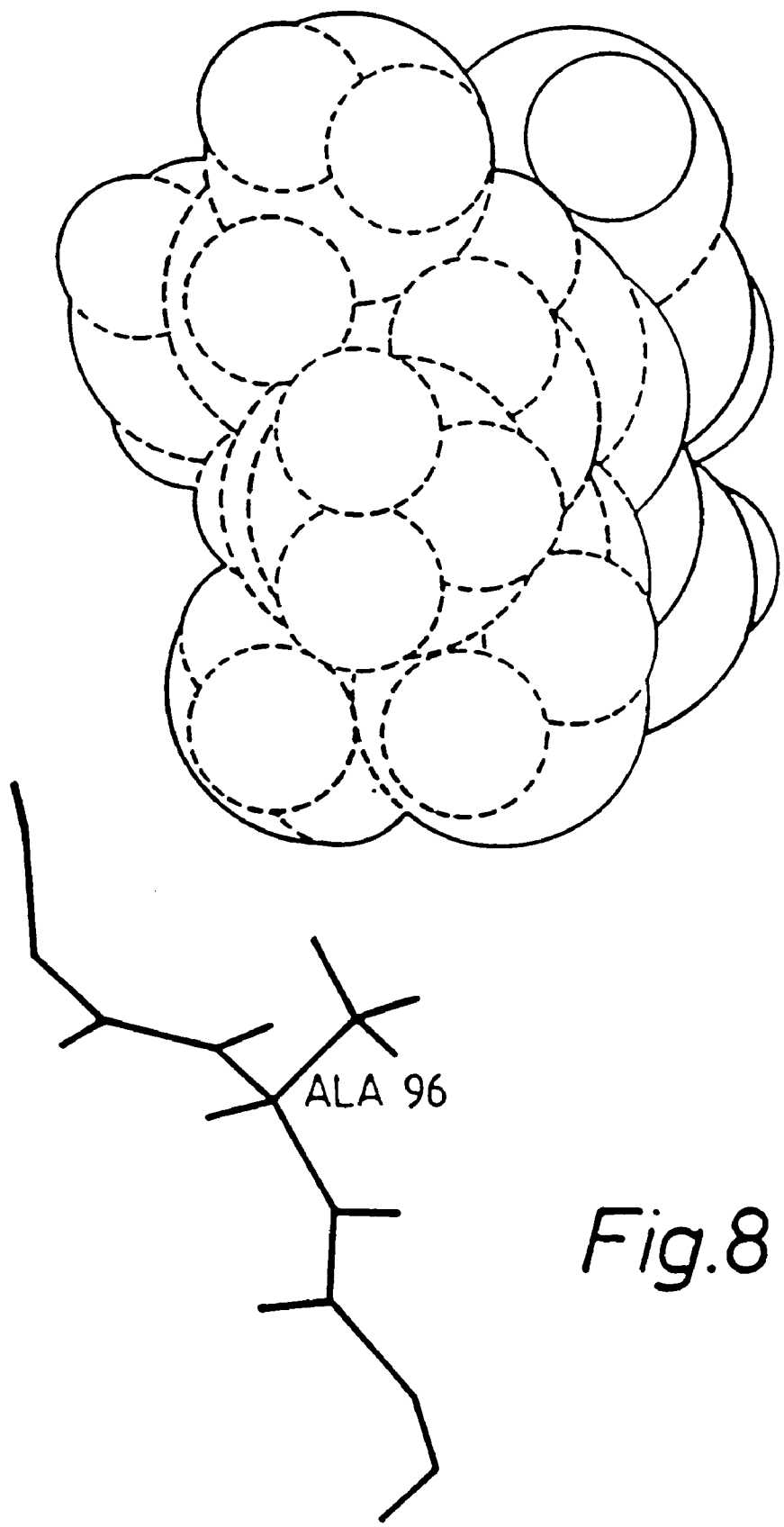
In FIG. 8 a molecular design picture is given, showing the musk odour molecule traseolide® and a modified musk antigen, described in Example 3.

Secondly, the binding site of the resulting Fv was mapped by visually docking the musk antigen into the CDR region, followed by a refinement using molecular dynamics again. Upon inspection of the resulting model for packing efficiency (van der Waals contact areas), it was concluded that substitution of ALA H96 by VAL would increase the (hydrophobic) contact area between the ligand and Fv, and consequently lead to a stronger interaction (see FIG. 8).

When this mutation is introduced into M02/01/01, the cDNA-derived scFv from Example 2, the result will be Fv M020501i; a variant with an increased affinity of at least a factor of 5 can be expected, and the increased affinity could be measured using fluorescence titration of the Fv with the musk odour molecule.

EXAMPLE 4

Construction of a Gene Encoding a Chimeric Protein That Will Be Anchored in the Cell Wall of Lower Eukaryote and is Able to Bind Hormones Such as HCG Gene fragments, encoding the variable regions of the heavy and light chain fragments from the monoclonal antibody directed against the human chorionic gonadotropin were obtained from a hybridoma cell line in a similar way as described in Example 2.

Subsequently, these HCG $V_H$ and $V_L$ gene fragments were cloned into plasmid pUR4143 by replacing the corresponding PstI-BstEII and SacI-XhoI gene fragments, resulting in plasmid pUR4146.

Figure 9:
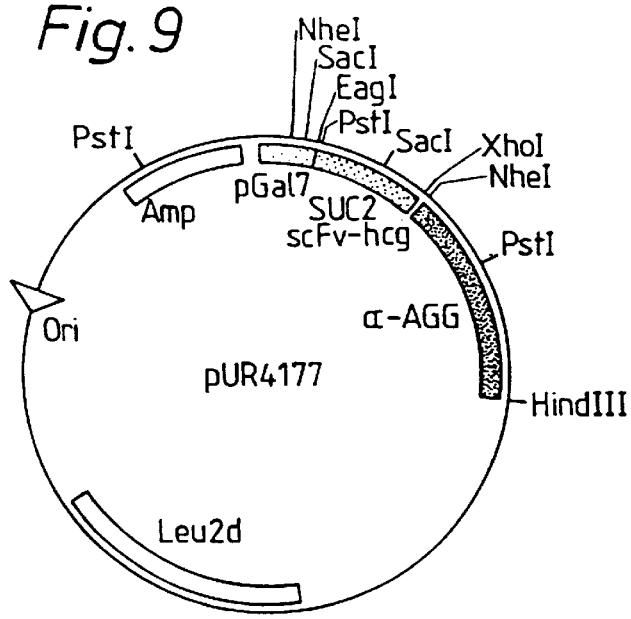
In FIG. 9 the composition of plasmid pUR4177 is indicated. Its construction is described in Example 4. Plasmid pUR4177 contains the 734 bp EagI-XhoI DNA fragment given in SEQ ID NO: 13 encoding the variable regions of the heavy and light chain fragments from the monoclonal antibody directed against the human chorionic gonadotropin (an scFv-HCG fragment) and is a 2 μm-based vector suitable for production of the chimeric scFv HCG-αAGG fusion protein preceded by the invertase signal sequence and under the control of the GAL7 promoter.
Figure 10:
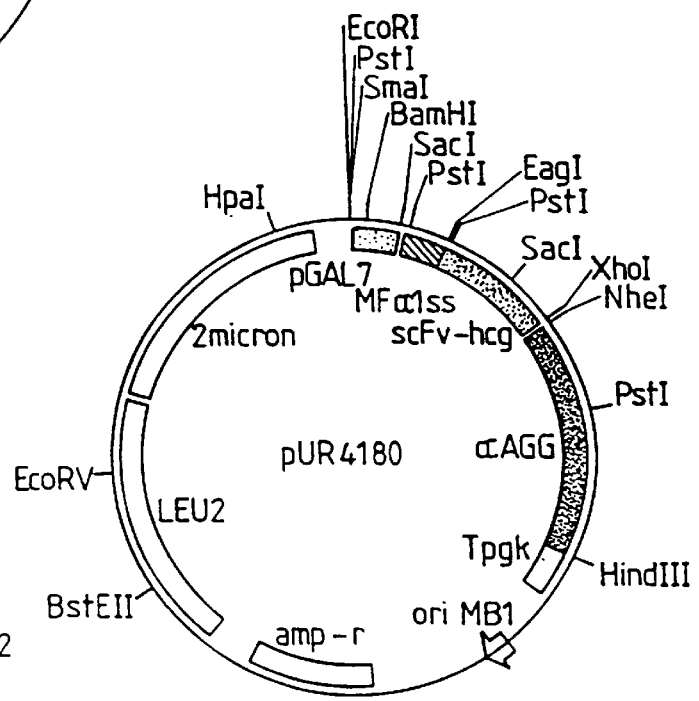
In FIG. 10 the composition of plasmid pUR4180 is indicated. Its preparation is indicated in Example 4. It contains the above mentioned 734 bp EagI-XhoI DNA fragment given in SEQ ID NO: 13 and is a 2 μm-based vector suitable for production of the chimeric scFv-HCG-αAGG fusion protein preceded by the prepro-α-mating factor signal sequence and under the control of the GAL7 promoter.

Similar to the method described in Example 2, the 734 bp EagI-XhoI fragment (nucleotide sequence given in SEQ ID NO: 13) encoding the variable regions of the heavy and light chain fragments from the monoclonal antibody directed against the human chorionic gonadotropin (an scFv-HCG fragment) was isolated from pUR4146 and was introduced into the vector backbone fragment of pUR4178 (see Example 2) and will be introduced into the vector backbone fragment of pUR4175 (see Example 1), both digested with the same restriction enzymes. The resulting plasmids pUR4177 (see FIG. 9) was, and pUR4180 (see FIG. 10) will be, introduced into S. cerevisiae strain SU10.

EXAMPLE 5

Construction of a Gene Encoding a Chimeric scFv-FLO1 Protein That Will Be Anchored in the Cell Wall of Lower Eukaryote and is Able to Bind Hormones Such as HCG One of the genes associated with the flocculation phenotype in S. cerevisiae is the FLO1 gene. The DNA sequence of a clone containing major parts of the FLO1 gene has been determined, see SEQ ID NO: 14 giving 2685 bp of the FLO1 gene. The cloned fragment appeared to be approximately 2 kb shorter than the genomic copy as judged from Southern and Northern hybridizations, but encloses both ends of the FLO1 gene. Analysis of the DNA sequence data indicates that the putative protein contains at the N-terminus a hydrophobic region which confirms a signal sequence for secretion, a hydrophobic C-terminus that might function as a signal for the attachment of a GPI-anchor and many glycosylation sites, especially in the C-terminus, with 46.6% serine and threonine in the arbitrarily defined C-terminus (aa 271-894). Hence, it is likely that the FLO1 gene product is located in an orientated fashion in the yeast cell wall and may be directly involved in the process of interaction with neighbouring cells.

The cloned FLO1 sequence might therefore be suitable for the immobilization of proteins or peptides on the cell surface by a different type of cell wall anchor.

Figure 11:
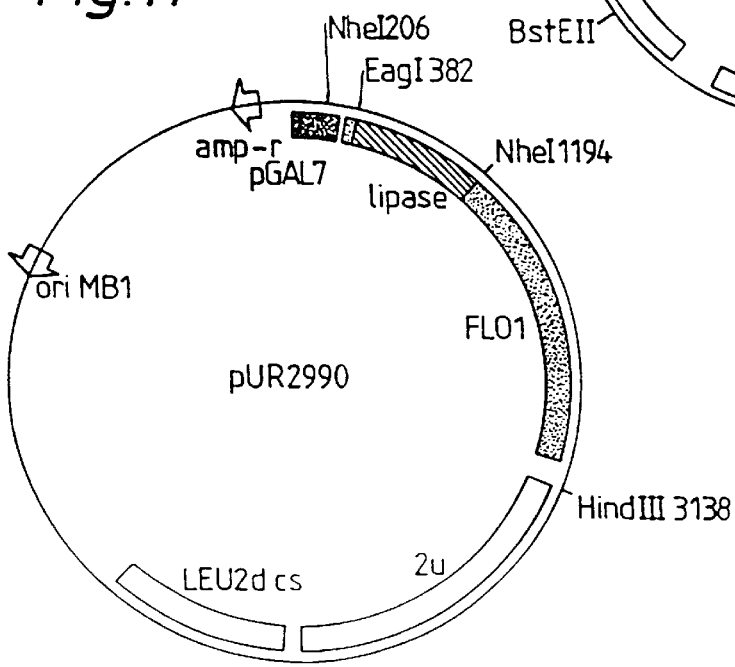
In FIG. 11 the composition of plasmid pUR2990, a 2 μm-based vector, is indicated, which is suggested in Example 5 as a starting vector for the preparation of plasmid pUR4196 (see FIG. 12). Plasmid pUR2990 contains a DNA fragment encoding a chimeric lipase-FLO1 protein that will be anchored in the cell wall of a lower eukaryote and can catalyze lipid hydrolysis.
Figure 12:
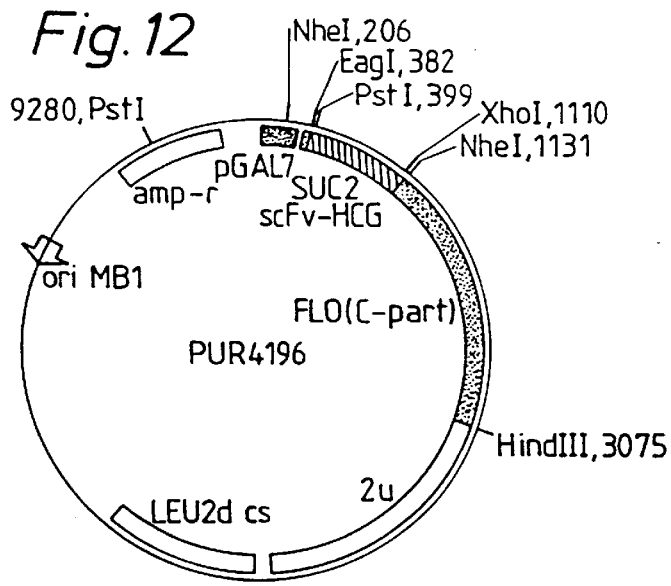
In FIG. 12 the composition of plasmid pUR4196 is indicated. Its preparation is explained in Example 5. It contains a DNA fragment encoding a chimeric protein comprising the scFv-HCG followed by the C-terminal part of the FLO1-protein, and is a vector suitable for the production of a chimeric protein anchored in the cell wall of the host organism and can bind HCG.

For the production of a chimeric protein comprising the scFv-HCG followed by the C-terminal part of the FLO1-protein, plasmid pUR2990 (see FIG. 11) can be used as a starting vector. The preparation of episomal plasmid pUR2990 was described in our co-pending patent application WO-94/01567 (UNILEVER) published on Jan. 20, 1994, i.e. during the priority year. Plasmid pUR2990 comprises the chimeric gene consisting of the gene encoding the Humicola lipase and a gene encoding the putative C-terminal cell wall anchor domain of the FLO1 gene product, the chimeric gene being preceded by the invertase signal sequence (SUC2) and the GAL7 promoter; further the plasmid comprises the yeast 2 μm sequence, the defective Leu2 promoter described by Eckard and Hollenberg (1983), and the Leu2 gene, see Roy c.s. (1991). Plasmid pUR4146, described in Example 4, can be digested with PstI and XhoI, and the about 0.7 kbp PstI-XhoI fragment containing the scFv-HCG coding sequence can be isolated. For the in frame fusion of this DNA sequence between the C-terminal FLO1 part and the SUC2 signal sequence, the fragment can be directly ligated with the 9.3 kbp EagI/NheI (partial) backbone of plasmid pUR2990, resulting in plasmid pUR4196 (see FIG. 12). This plasmid will comprise an additional triplet encoding Ala at the transition between the SUC2 signal sequence and the start of the scFv-HCG, and a E-I-K-G-G amino acid sequence in front of the first amino acid (Ser) of the C part of FLO1 protein.

If in the previous Examples 1–5 the level of exposed antibody fragments is too low, the production level can be increased by mutagenesis of the frame work regions of the antibody fragment. This can be done in a site directed way or by (targeted) random mutagenesis, using techniques described in the literature.

EXAMPLE 6

Construction of a Gene Encoding a Chimeric Protein That Will Be Anchored in the Cell Wall of a Lower Eukaryote and is Able to Bind Cholesterol In the literature two DNA sequences for cholesterol oxidase are described, the choB gene from Brevibacterium

*sterolicum*, see Ohta c.s. (1991) and the choA gene from *Streptomyces sp.* SA-COO, see Ishizaka c.s. (1989). For the construction of a DNA fusion between the choB gene coding for cholesterol oxidase (EC 1.1.3.6) and the 3' part of the AG-α1 gene, the PCR technique on chromosomal DNA can be applied. Chromosomal DNA can he isolated by standard techniques from *Brevibacterium sterolicum*, and the DNA part coding for the mature part of the cholesterol oxidase can be amplified through application with the following corresponding PCR primers cho01pcr and cho02pcr:

domain with the Gly-X-Gly-X-X-Gly sequence near the N-terminus (amino acid 18–23). Site-directed in vitro mutagenesis on the plasmid pUR2985 according to the manufacturer's protocol (Muta-Gene kit, Bio-Rad) can be applied to inactivate the FAD-binding site through replacing the triplet(s) encoding the Gly residue(s) by triplets encoding other amino acids, thereby presumably inactivating the enzyme. E.g. the following primer can be used for site-directed mutagenesis of 2 of the conserved Gly residues.

```
cho01pcr
5'-                              GCC CCC AGC CGC ACC CTC G-3'  = SEQ ID NO: 16
3'-                              CGG GGG TCG GCG TGG GAG C-5'  = SEQ ID NO: 17
                                 ||| ||| ||| ||| ||| ||| |
5'-AGATCTGAATTCGCGGCC            GCC CCC AGC CGC ACC CTC G-3'  = SEQ ID NO: 18
         EcoRI NotI
                EagI cho02pcr
                                       NheI   HindIII
3'-TAG TAG AGC AGG CTG TAG GTC CGATCGACTTTCGAATCTAGA-5' = SEQ ID NO: 19
   ||| ||| ||| ||| ||| ||| |||
5'-ATC ATC TCG TCC GAC ATC CAG-3' =                       SEQ ID NO: 20
3'-TAG TAG AGC AGG CTG TAG GTC-5' =                       SEQ ID NO: 21
```

Figure 13:
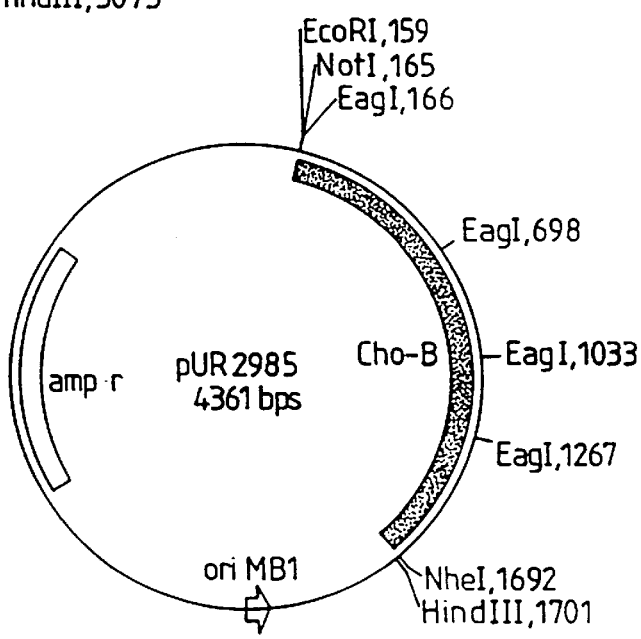
In FIG. 13 the composition of plasmid pUR2985 is indicated. Its preparation is described in Example 6. It contains a choB gene coding for the mature part of the cholesterol oxidase (EC 1.1.3.6) obtained via PCR techniques from the chromosome of Brevibacterium sterolicum.

Both primers can specifically hybridize with the target sequence, thereby amplifying the coding part of the gene in such a way, that the specific PCR product—after Proteinase K treatment and digestion with EcoRI and HindIII—can be directly cloned into a suitable vector, here preferably pTZ19R, see Mead c.s. (1986). This will result in plasmid pUR2985 (see FIG. 13).

In addition to the already mentioned restriction sites both PCR primers generate other restriction sites at the 5' end and the 3' end of the 1.5 kbp DNA fragment, which can be used later on to fuse the fragment in frame between either the SUC2 signal sequence or the prepro-α-mating factor signal sequence on one side and the C-terminus coding part of the α-agglutinin gene on the other side. To facilitate the ligation behind the prepro-MF sequence a NotI site is introduced at the 5' end of PCR oligonucleotide cho01pcr, allowing for example, the exchange of the 731 bp EagI/NheI fragment containing the scFv-Lys coding sequence in pUR4175 for the choB coding sequence.

To create an enzymatically inactive fusion protein between cholesterol oxidase and α-agglutinin, the above described subcloning into pTZ19R can be used. Cholesterol oxidase is an FAD-dependent enzyme for which the crystal structure of the *Brevibacterum sterolicum* enzyme has been determined, see Vrielink c.s. (1991). The enzyme displays homology with the typical pattern of the FAD-binding

```
pr 3'- CGG GAG CAG TAG CGG TCA CGT ATG CCG CCA CGG CAG CGG CGC -5'
       ||| ||| ||| ||| | | ||| | ||| ||| ||| ||| ||| ||| |||
cs 5'- GCC CTC GTC ATC GGC AGT GGA TAC GGC GGT GCC GTC GCC GCG -3'
        Ala         Gly    Gly        Gly Gly Ala     Ala Ala
                     ↓      ↓
                    Ala    Ala
pr = primer =             SEQ ID NO: 22
cs = coding strand =      SEQ ID NO: 23
```

Figure 14:
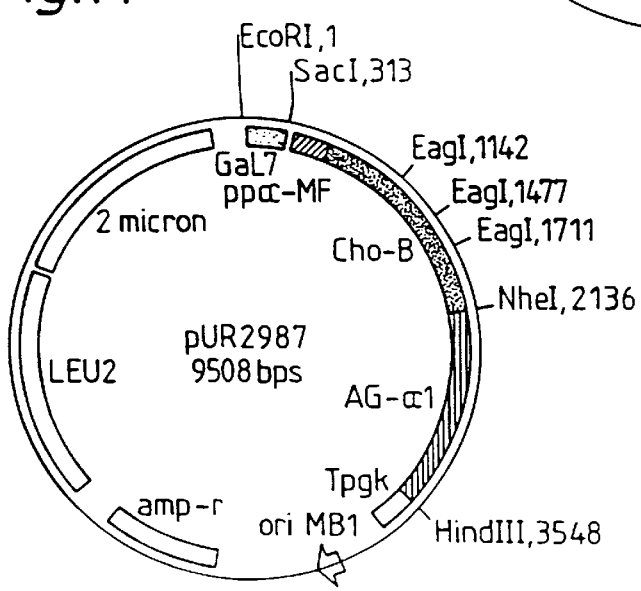
In FIG. 14 the composition of plasmid pUR2987 is indicated. Its preparation from plasmid pUR2985 is described in Example 6. It contains a DNA sequence comprising the choB gene coding for the mature part of the cholesterol oxidase preceded by DNA encoding the prepro-α-mating factor signal sequence and followed by DNA encoding the C-terminal part of α-agglutinin.

As a result of the mutagenesis with the described primer, plasmid pUR2986 will be obtained. From this plasmid the DNA coding for the presumably inactivated cholesterol oxidase can be released as a 1527 bp fragment through NotI/NheI digestion, and subsequently directly used to exchange the scFv-Lys coding sequence in pUR4175, thereby generating plasmid pUR2987 (see FIG. 14). To obtain a variant yeast secretion vector, where the secretion is directed through the SUC2 signal sequence, for example the 1823 bp long SacI/NheI segment of plasmid pUR2986 can be used to replace the SacI/NheI fragment in pUR4174.

This inactivation of the FAD-binding site might be preferable over other mutations, since an unchanged active centre can he expected to leave the binding properties of cholesterol oxidase for cholesterol unaltered. Instead of the described Gly→Ala exchanges at position 18 and 20 of the mature coding sequence, every other suitable amino acid change can also be performed.

To inactivate the enzyme, site directed mutagenesis can be optionally immediately performed in the active site cavity, for example through exchange of the Glu331, a residue appropriately positioned to act as the proton acceptor, thus generating a new variant of an immobilized, enzymatically inactive fusion protein.

EXAMPLE 7
Construction of a Gene Encoding a Chimeric Protein That Will Be Anchored in the Cell Wall of a Lactic Acid Bacterium and is Able to Bind Cholesterol It has been described that proteinase of *Lactococcus lactis* subsp. *cremoris* is anchored to the cell wall through its 127 amino acid long C-terminal, see Kok c.s. (1988) and Kok (1990). In a way similar to that described in Example 6, the cholesterol oxidase of *Brevibacterium sterolicum* (choB) can be immobilized on the surface of *Lactococcus lactis*. Fusions can be made can be made between the choB structural gene and the N-terminal signal sequence and the C-terminal anchor of the proteinase of *Lactococcus lactis*. Plasmid pGKV550 (see FIG. 15) contains the complete proteinase operon of *Lactococcus lactis* subsp. *cremoris* Wg2, including the promoter, a ribosome binding site and DNA fragments encoding the already mentioned signal and anchor sequences, see Kok (1990). First a DNA fragment, containing the main part of the signal sequence, flanked by a ClaI site and an EagI site can be constructed with PCR on pGKV550 as follows:

```
Primer prt1:
    5'-AA GAT CTA TCG ATC TTG TTA GCC GGT ACA-3' =           SEQ ID NO: 24
Proteinase gene (non coding strand):
    3'-TT CCC GAT AGC TAG AAC AAT CGG CCA TGT CAG-5' =       SEQ ID NO: 25
              ClaI Proteinase gene:     Gln Ala Lys
    5'-GTC GGC GAA ATC CAA GCA AAG GCG GCT-3' =              SEQ ID NO: 26
Primer prt2:
    3'-CAG CCG CTT TAG GTT CGT TGC CGG CCC CCC TTC GAA CCC-5' = SEQ ID NO: 27
                              EagI          HindIII
```

After the PCR reaction as described in Example 6, the 98 bp long PCR fragment can be isolated and digested with ClaI and HindIII. pGKV550 can subsequently be cleaved partially with ClaI and completely with HindIII, after which digestions the vector fragment, containing the promoter, the ribosome binding site, the DNA fragment encoding the N-terminal 8 amino acids and the cell wall binding fragment containing the 127 C-terminal amino acids of the proteinase gene can be isolated on gel.

A copy of the cholesterol oxidase gene, suitable for fusion with the prtP anchor domain can be produced by a PCR reaction using plasmid pUR2985 (Example 6) as template and a combination of primer cho01pcr (see Example 6) and the following primer cho03pcr instead of primer cho02pcr:

unlikely that the Lactococcus will secrete FAD as well, the cholesterol oxidase will not be active but will be capable to bind cholesterol.

EXAMPLE 8

Construction of a Gene Encoding a Chimeric Protein That Will Be Anchored in the Cell Wall of a Lower Eukaryote and is Able to Bind Growth Hormones, such as the Epidermal Growth Factor For the isolation of larger amounts of human epidermal growth factor (EGF) the corresponding receptor can be used in form of a fusion between the binding domain and a C-terminal part of α-agglutinin as cell wall anchor. The complete cDNA sequence of the human epidermal growth factor is cloned and sequenced. For the construction of a fusion protein with EGF binding capacity the N-terminal part of the mature receptor until the central 23 amino acids transmembrane region can be utilized.

The plasmid pUR4175 can be used for the construction. Through digestion with EagI and NheI (partial) a 731 bp DNA fragment containing the sequence coding for scFv is released and can be replaced by a DNA fragment coding for the first 621 amino acids of human epidermal growth factor receptor. Initiating from an existing human cDNA library or otherwise through production of a cDNA library by standard techniques from preferentially EGF receptor overexpressing cells, e.g. A431 carcinoma cells, see Ullrich c.s. (1984), further PCR can be applied for the generation of in frame

```
cho03pcr                              HindIII
3'-TAG TAG AGC AGG CTG TAG GTC CGA GTT CGA ACC TAG GC-5' =   SEQ ID NO: 40
   ||| ||| ||| ||| ||| ||| |||
5'-ATC ATC TCG TCC GAC ATC CAG =                              SEQ ID NO: 20.
```

Figure 16:
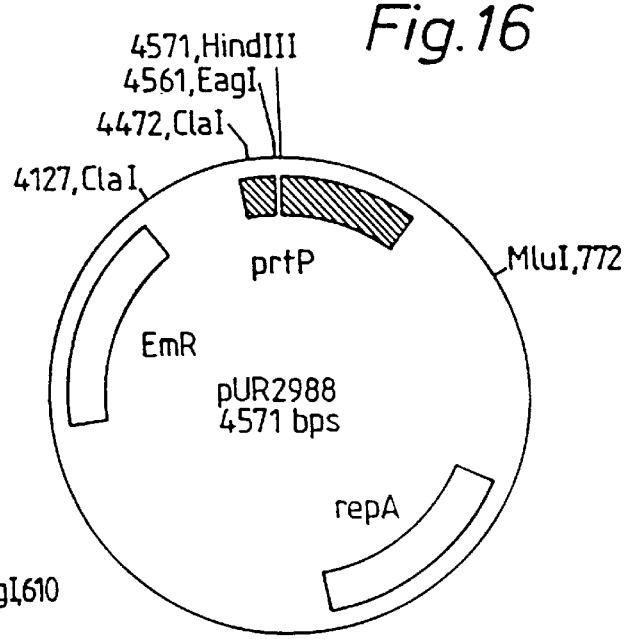
In FIG. 16 the composition of plasmid pUR2988 is indicated. Its preparation is indicated in Example 7. It is anticipated that this plasmid can be used for preparing a further plasmid pUR2989, which after introduction in a lactic acid bacterium will be responsible for producing a chimeric protein that will be anchored at the outer surface of the lactic acid bacterium and is capable of binding cholesterol.

The about 1.53 kbp fragment generated by this reaction can be digested with NotI and HindIII to produce a molecule which can subsequently be ligated with the large EagI/HindIII fragment from pUR2988 (see FIG. 16). The resulting plasmid, pUR2989, will contain the cholesterol oxidase coding sequence inserted between the signal sequence and the C-terminal cell wall anchor domain of the proteinase gene. After introduction into *Lactobacillus lactis* subsp. *lactis* MG 1363 by electroporation, this plasmid will express cholesterol oxidase under control of the proteinase promoter. The transport through the membrane will be mediated by the proteinase signal sequence and the immobilization of the cholesterol oxidase by the proteinase anchor. As it is linkage between the extracellular binding domain of the human growth factor receptor (amino acid 1–622) and the C-terminal part of α-agglutinin.

PCR oligonucleotides for the in frame linkage of human epidermal growth factor receptor and the C-terminus of α-agglutinin.

a: PCR oligonucleotides for the transition between SUC2 signal sequence and the N-terminus of mature EGF receptor.

```
                              >mature EGF receptor
             pri EGF1:        Ala Leu Glu     Lys Lys Val =    SEQ ID NO: 28
```

```
                              -continued
     5'-GGG GCG GCC GCG CTG GAG GAA AAG AAA GTT TGC-3'
             NotI         ||| ||| ||| ||| ||| ||| |||
     3'-CGC TCA GCC CGA GAC CTC CTT TTC TTT CAA ACG 5'
   EGF rec (non-coding strand): =                         SEQ ID NO: 29
``` b: PCR oligonucleotides for the in frame transition between C terminus of the extracellular binding domain of EGF receptor and the C terminal part of α-agglutinin.

```
   EGF rec (coding strand):
       Asn Gly Pro     Ile Pro Ser    Ala Thr
   5'-AAT GGG CCT AAG ATC CCG TCC ATC GCC ACT-3' =          SEQ ID NO: 30
      ||| ||| ||| ||| ||| ||| |||
   3'-TTA CCC GGA TTC TAG GGC AGG CGA TCGGAATTCGAA CCCC-5' = SEQ ID NO: 31
   pr EGF2:                            NheI  HindIII
```

This fusion would result in an addition of 2 Ala amino acids between the signal sequence and the mature N-terminus of EGF receptor.

Figure 17:
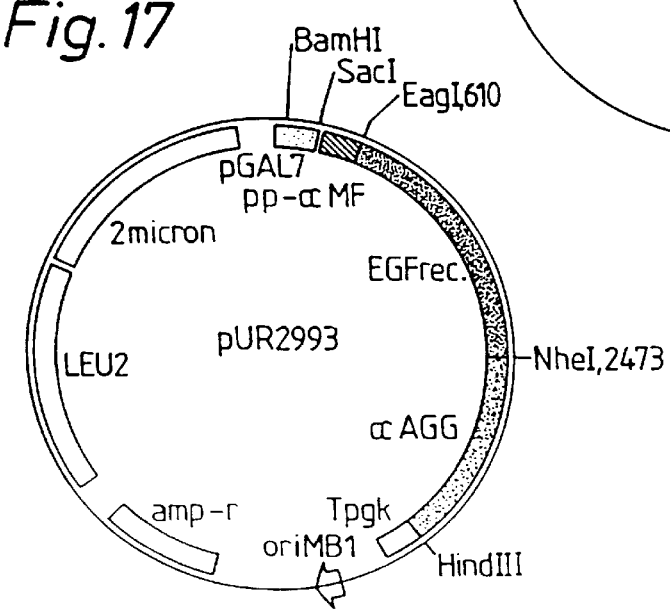
In FIG. 17 the composition of plasmid pUR2993 is indicated. Its preparation is described in Example 8. It is anticipated that this plasmid can be used for transforming yeast cells that can bind a human epidermal growth factor (EGF) through an anchored chimeric protein containing an EGF receptor.

The newly obtained 1.9 kbp PCR fragment can be digested with NotI and NheI and directly ligated into the vector pUR4175 after digesting with the same enzymes, resulting in plasmid pUR2993 (see FIG. 17), comprising the GAL7 promoter, the prepro-α-mating factor sequence, the chimeric EGF receptor binding domain gene/α-agglutinin gene, the yeast 2 μm sequence, the defective LEU2 promoter and the LEU2 gene. This plasmid can be transformed into *S. cerevisiae* and the transformed cells can be cultivated in YP medium whereby expression of the chimeric protein can be induced by adding galactose to the medium.

EXAMPLE 9

Construction of Genes Encoding a Chimeric Protein Anchored to the Cell Wall of Yeast, Comprising a Binding Domain of a "Camelidae" Heavy Chain Antibody Recently it was described that camels as well as a number of related species (e.g. lamas) contain a considerable amount of IgG antibody molecules which are only composed of heavy-chain dimers, see Hamers-Casterman c.s. (1993). Although these "heavy-chain" antibodies are devoid of light chains, it was demonstrated, that they nevertheless have an extensive antigen-binding repertoire. In order to show that the variable regions of this type of antibodies can be produced and will be linked to the exterior of the cell wall of a yeast, the following constructs were prepared.

Construction of pUR2997, pUR2998 and pUR2999

The about 2.1 kbp EagI-HindIII fragment of pUR4177 (Example 4, FIG. 9) was isolated. By using PCR technology, an EcoRI restriction site was introduced immediately upstream of the EagI site, whereby the C of the EcoRI site is the same as the first C of the EagI site. The thus obtained EcoRI-HindIII fragment was ligated into plasmid pEMBL9, which was digested with EcoRI and HindIII, which resulted in pUR4177.A The EcoRI/NheI fragment of plasmid pUR4177.A was replaced by the EcoRI/NheI fragments of three different synthetic DNA fragments (SEQ ID NO: 32, SEQ ID NO: 33, and SEQ ID NO: 34) resulting in pUR2997, pUR2998 and pUR2999, respectively. The about 1.5 kbp BstEII-HindIII fragments of pUR2997 and pUR2998 were isolated.

Construction of pUR4421

The multiple cloning site of plasmid pEMBL9, see Dente c.s. (1983), (ranging from the EcoRI to the HindIII site) was replaced by a synthetic DNA fragment having the nucleotide sequence given below, see SEQ ID NO: 35 giving the coding strand and SEQ ID NO: 36 giving the non-coding strand. The 5'-part of this nucleotide sequence comprises in EagI site, the first 4 codons of a Camelidae $V_H$ gene fragment (nucleotides 16–27) and a XhoI site (CTCGAG) coinciding with codons 5 and 6 (nucleotides 28–33). The 3'-part comprises the last 5 codons of the Camelidae $V_H$ gene (nucleotides 46–60) (part of which coincides with a BstEII site), eleven codons of the Myc tail (nucleotides 61–93), see SEQ ID NO: 35 containing these eleven codons and SEQ ID NO: 37 giving the amino acid sequence, and an EcoRI site (GAATTC). The EcoRI site, originally present in pEMBL9, is not functional any more, because the 5'-end of the nucleotide sequence contains AATTT instead of AATTC, indicated below as (EcoRI). The resulting plasmid is called pUR4421. The Camelidae $V_H$ fragment starts with amino acids Q-V-K and ends with amino acids V-S-S.

```
      (EcoRI) EagI                        XhoI              BstEII
   5'-AATTTAGCGG CCGCCCAGGT GAAACTGCTC GAGTAAGTGA CTAAGGTCAC- 50 = SEQ ID NO: 37
   3' 1   ATCGCC GGCGGGTCCA CTTTGACGAG CTCATTCACT GATTCCAGTG-
           5               Q  V  K

-CGTCTCCTCA GAACAAAAAC TCATCTCAGA AGAGGATCTG AATTAATGAG- 100
   -GCAGAGGAGT CTTGTTTTTG AGTAGAGTCT TCTCCTAGAC TTAATTACTC-
     V  S  S   E  Q  K   L  I  S  E   E  D  L   N  *  *

EcoRI              HindIII
   -AATTCATCAA ACGGTGATA      -3'      119 =           SEQ ID NO: 35
   -TTAAGTAGTT TGCCACTATT CGA -5'      123 =           SEQ ID NO: 36
```

Construction of pUR4424

After digesting the plasmid pB09 with XhoI and BstEII, a DNA fragment of about 0.34 kbp was isolated from agarose gel. This fragment codes for a truncated $V_H$ fragment, missing both the first 4 and the last 5 amino acids of the Camelidae $V_H$ fragment. Plasmid pB09 was deposited as *E. coli* JM109 pB09 at the Centraal Bureau voor Schimmelcultures, Baarn on Apr. 20, 1993 with deposition number CBS 271.93. The DNA and amino acid sequences of the Camel $V_H$ fragments followed by the Flag sequence as present in plasmid pB09 were given in FIG. 6B of European patent application 93201239.6 (not yet published), which is herein incorporated by reference. The obtained about 0.34 kbp fragment was cloned into pUR4421. To this end plasmid pUR4421 was digested with XhoI and HindIII, after which the about 4 kb vector fragment was isolated from an agarose gel. The resulting vector was ligated with the about 0.34 kbp XhoI/BstEII fragment and a synthetic DNA linker having the following sequence:

```
BstEII              HindIII
  GTCACCGTCTCCTCATAATGA    = SEQ ID NO: 38
       GCAGAGGAGTATTACTTCGA = SEQ ID NO: 39
``` resulting in plasmid pUR4421-09.

Plasmid pSY16 was digested with EagI and HindIII, after which the about 6.5 kbp long vector backbone was isolated and ligated with the about 0.38 kbp EagI/HindIII fragment from pUR4421-09 resulting in pUR4424.

Construction of pUR4482 and pUR4483

From pUR4424 the about 0.44 kbp SacI-BstEII fragment, coding for the invertase signal sequence and the camel heavy chain variable 09 (=CH$_V$09) fragment, was isolated as well as the about 6.3 kbp SacI-HindIII vector fragment. The about 6.3 kbp fragment and the about 0.44 kbp fragment from pUR4424 were ligated with the BstEII-HindIII fragment from pUR2997 or pUR2998 yielding pUR4482 and pUR4483, respectively.

Plasmid pUR4482 is thus an yeast episomal expression plasmid for expression of a fusion protein with the invertase signal sequence, the CH$_V$09 variable region, the Myc-tail and the Camel "X-P-X-P" Hinge region, see Hamers-Casterman c.s. (1993), and the α-agglutinin cell wall anchor region. Plasmid pUR4483 differs from pUR4482 in that it contains the Myc-tail but not the "X-P-X-P" Hinge region. Similarly, the BstEII-HindIII fragment from pUR2999 can be ligated with the about 6.3 kbp vector fragment and the about 0.44 kbp fragment from pUR4424, resulting in pUR4497, which will differ from pUR4482 in that it contains the "X-P-X-P" Hinge region but not the Myc-tail.

The plasmids pUR4424, pUR4482 and pUR4483 were introduced into *Saccharomyces cerevisiae* SU10 by electroporation, and transformants were selected on plates lacking leucine. Transformants from SU10 with pUR4424, pUR4482 or pUR4483, respectively, were grown on YP with 5% galactose and analysed with immuno-fluorescence microscopy, as described in Example 1 of our co-pending WO-94/01567 (UNILEVER) published on Jan. 20, 1994. This method was slightly modified to detect the chimeric proteins, containing both the camel antibody and the Myc tail, present at the cell surface.

In one method a monoclonal mouse anti-Myc antibody was used as a first antibody to bind to the Myc part of the chimeric protein; subsequently a polyclonal anti-mouse Ig antiserum labeled with fluorescein isothiocyanate (=FITC) ex Sigma, Product No. F-0527, was used to detect the bound mouse antibody and a positive signal was determined by fluorescence microscopy.

In the other method a polyclonal rabbit anti-human IgG serum, which had earlier been proven to cross-react with the camel antibodies, was used as a first antibody to bind the camel antibody part of the chimeric protein; subsequently a polyclonal anti-rabbit Ig antiserum labeled with FITC ex Sigma, Product No. F-0382, was used to detect the bound rabbit antibody and a positive signal was determined by fluorescence microscopy.

The results in FIG. 19 and FIG. 20 show clearly that fluorescence can be observed on those cells in which a fusion protein of the CH$_V$09 fragment with the α-agglutinin cell wall anchor region is produced (pUR4482 and pUR4483). No fluorescence however, was visible on the cells which produce the CH$_V$09 fragment without this anchor (pUR4424), when viewed under the same circumstances.

Patent Literature References:

EP-A1-0255153 (UNILEVER) Production of guar alpha-galactosidase by hosts transformed by recombinant DNA methods. First priority date 03.06.86; published 03.02.88

WO-91/00920 (UNILEVER) Process for preparing a protein by a fungus transformed by multicopy integration of an expression vector. First priority date 07.07.89; published 24.01.91

WO-91/19782 (UNILEVER) Xylanase production. Priority date 19.06.90; published 26.12.91

WO-94/01567 (UNILEVER) Process for immobilizing enzymes to the cell wall of a microbial cell by producing a fusion protein. First priority date 08.07.92; published 20.01.94

EP patent application 93201239.6 (not yet published) Production of antibodies or (functionalized) fragments thereof derived from heavy chain immunoglobulins of Camelidae. Filing date 29.04.9.

Non-Patent Literature References:

R. E. Bird & B. Webb Walker Single chain antibody variable regions. TIBTECH 9 (April 1991) 192–137

A. Conzelmann, C. Fankhauser & C. Desponds Myoinositol gets incorporated into numerous membrane glycoproteins of *Saccharomyces cerevisiae*; incorporation is dependent on phosphomannomutase (SEC53). The EMBO Journal 9, No.3 (1990) 653–661.

L. Dente, G. Cesareni & R. Cortese pEMBL: a new family of single stranded plasmids. Nucleic Acids Research 11, No. 6 (1983) 1645–1655

E. Erhart, & C. P. Hollenberg The Presence of a Defective Leu2 Gene on 2μ DNA Recombinant Plasmids of *Saccharomyces cerevisiae* Is Responsible for Curing and High Copy Number. Journal of Bacteriology. 156, No.2 (November 1983) 625–635

C. Hamers-Casterman, T. Atarhouch, S. Muyldermans, G. Robinson, C. Hamers, E. Bajyana Songa, N. Bendshman & R. Hamers Naturally occurring antibodies devoid of light chains. Nature 363 (Jun. 3, 1993) 446–448.

M. M. Harmsen, A. C. Langedijk, E. van Tuinien, R. H. Geerse, H. A. Rauè, & J. Maat Effect of pmr1 disruption and different signal sequences on the intracellular processing and secretion of *Cyamopsis tetragonoloba* α-galactosidase by *Saccharomyces cerevisiae*. Gene 125 ( 1993) 115–123

T. Ishizaki, N. Hirayama, H. Shinkawa, O. Nimi, & Y. Murooka Nucleotide Sequence of the Gene for Cholesterol Oxidase from a *Streptomyces sp*. Journal of Bacteriology 171, No.1 (January 1989) 596–601

J. Kok, K. J. Leenhouts, A. J. Haandrikman, A. M. Ledeboer & G. Venema Nucleotide Sequence of the Cell Wall Proteinase Gene of *Streptococcus cremoris* Wg2. Applied and Environmental Microbiology 54, No. 1 (January 1988) 231–238

J. Kok Genetics of the proteolytic system of lactic acid bacteria. FEMS Microbiology Reviews. 87 (1990) 15–42, esp. item 3.2 and FIG. 7 on pages 22–23

R. Lewin The universal constructor set. New Scientist (Dec. 8, 1990) 30–33

P. N. Lipke, D. Wojciechowicz & J. Kurjan AGa1 Is the Structural Gene for the *Saccharomyces cerevisiae* α-Agglutinin, a Cell Surface Glycoprotein Involved in Cell-Cell Interactions during Mating. Molecular and Cellular Biology. 9, No. 8 (August 1989) 3155–3165.

D. A. Mead, E. Szczesna-Skorupa & B. Kemper Single-stranded DNA 'blue' T7 promoter plasmids: a versatile tandem promoter system for cloning and protein engineering. Protein Engineering 1, No. 1 (1986) 67–74

R. Orlandi, D. H. Güssow, P. T. Jones, & G. Winter Cloning immunoglobulin variable domains for expression by the polymerase chain reaction. Proc. Natl. Acad. Sci. USA 86 (May 1989) 3833–3837

B. C. Ossendorp The non-specific lipid-transfer binding protein: a recombinant DNA and immunological approach. Thesis University of Utrecht (Sep. 30, 1992)

T. Ohta, K. Fujishiro, K. Yamaguchi, Y. Tamura, K. Aisaka, T. Uwajima & M. Hasegawa Sequence of gene choB encoding cholesterol oxidase of *Brevibacterium sterolicum*: comparison with choA of *Streptomyces sp.* SA-COO. Gene 103 (1991) 93–96

A. Roy, C. F. Lu, D. L. Marykwas, P. N. Lipke & J. Kurjan The AGA1 Product Is Involved in Cell Surface Attachment of the *Saccharomyces cerevisiae* Cell Adhesion Glycoprotein a-Agglutinin. Molecular and Cellular Biology 11 No. 8 (August 1991) 4196–4206

M. P. Schreuder, S. Brekelmans, H. van den Ende, & F. M. Klis Targeting of a Heterologous Protein to the Cell Wall of *Saccharomyces cerevisiae*. Yeast 9 (1993) 399–409

A. Ullrich, L. Coussens, J. S. Hayflick, T. J. Dull, A. Gray, A. W. Tam, J. Lee, Y. Yarden, T. A. Libermann, J. Schlessinger, J. Downward, E. L. V. Mayes, N. Whittle, M. D. Waterfield & P. H. Seeburg Human epidermal growth factor receptor cDNA sequence and aberrant expression of the amplified gene in A431 epidermal carcinoma cells. Nature 309 (May 31, 1984) 418–425.

J. M. A. Verbakel Heterologous gene expression in the yeast *Saccharomyces cerevisiae*. Thesis University of Utrecht (May 1, 1991), esp. pages 76–89

A. Vrielink, L. F. Lloyd, & D. M. Blow Crystal Structure of Cholesterol Oxidase from *Brevibacterium sterolicum* Refined at 1.8 Å Resolution. J. Mol. Biol., 219 (1991) 533–554

E. S. Ward, D. Güssow, A. D. Griffiths, P. T. Jones & G. Winter. Binding activities of a repertoire of single immunoglobulin variable domains secreted from *E. coli*. Nature 341 (Oct. 12, 1989) 544–546

Information on a deposit of a micro-organism under the Budapest Treaty is given above. In agreement with Rule 28 (4) EPC, or a similar arrangement for a State not being a Contracting State of the EPC, it is hereby requested that a sample of such deposit, when requested, will be submitted to an expert only.

We claim:

1. A method for immobilizing a binding protein or a functional part thereof, which binding protein or functional part thereof specifically binds to a compound, wherein said binding protein or functional part thereof is immobilized by being anchored to the cell wall of a fungus selected from the group consisting of yeasts and molds, said method comprising
recombinantly modifying said fungus to produce a chimeric protein, which chimeric protein comprises
said binding protein or functional part thereof,
a secretory signal peptide operably linked to said binding protein or functional part thereof and
a C-terminal anchoring part of a fungal cell wall anchoring protein operably linked to said binding protein or functional part thereof,
wherein, when said chimeric protein is produced, said chimeric protein is transported to said cell wall by said signal peptide and said C-terminal anchoring part is anchored to said cell wall, thereby immobilizing said binding protein or a functional part thereof.

2. The method of claim 1 wherein said fungus is selected from the group consisting of yeasts belonging to the genera Candida, Debaryomyces, Hansenula, Kluyveromyces, Pichia and Saccharomyces, and molds belonging to the genera Aspergillus, Penicillium and Rhizopus.

3. A fungus selected from the group consisting of yeasts and molds, wherein said fungus comprises a polynucleotide which comprises an open reading frame than encodes a chimeric protein, wherein said protein when produced is immobilized by being covalently linked to the cell wall of said fungus, said chimeric protein comprising:

(i) a binding protein, or a functional part thereof, which binding protein or functional part thereof specifically binds to a compound,
(ii) a secretory signal peptide operably linked to said binding protein or functional part thereof, and
(iii) a C-terminal anchoring part of a fungal cell wall anchoring protein operably linked to said binding protein or functional part thereof,
said open reading frame being operably linked to a promoter such that said chimeric protein is produced in said fungus, wherein said chimeric protein is transported to said cell wall by said signal peptide and said C-terminal anchoring part is covalently linked to said cell wall.

4. The fungus of claim 3, wherein said signal peptide is a signal peptide of a protein selected from the group consisting of the α-mating factor of yeast, α-agglutinin of yeast, a-agglutinin of yeast, invertase of Saccharomyces, inulinase of Kluyveromyces, α-amylase of Bacillus, and proteinases of lactic acid bacteria.

5. The fungus of claim 3, wherein said anchoring protein is selected from the group consisting of α-agglutinin, a-agglutinin, flocculation protein, and Major Cell Wall Protein of a fungus selected from the group consisting of yeasts and molds.

6. A process for separation of a target compound from a medium containing said target compound using a fungus according to claim 3, wherein said chimeric protein produced by said fungus comprises a binding protein or functional part thereof which specifically binds to said target compound, said process comprising contacting said medium containing said target compound with said fungus, under conditions such that said target compound specifically binds to said binding protein or functional part thereof, and separating said fungus from said medium, whereby said target compound which is bound to said binding protein or functional part thereof is separated from said medium with said fungus.

7. A method according to claim 1 wherein said fungus is a yeast.

8. A fungus according to claim 3 which is a yeast.

* * * * *